(12) United States Patent
Anselm et al.

(10) Patent No.: US 9,290,467 B2
(45) Date of Patent: Mar. 22, 2016

(54) CYCLIC AMIDES

(71) Applicant: Hoffmann-La Roche Inc., Nutley, NJ (US)

(72) Inventors: Lilli Anselm, Binzen (DE); David Banner, Basel (CH); Jean-Baptiste Blanc, Westfield, NJ (US); Delphine Gaufreteau, Bartenheim (FR); Wolfgang Haap, Loerrach (DE); Guido Hartmann, Loerrach (DE); Bernd Kuhn, Reinach (CH); Thomas Luebbers, Loerrach (DE); Jens-Uwe Peters, Grenzach-Wyhlen (DE); Beat Spinnler, Allschwil (CH)

(73) Assignee: HOFFMANN—LA ROCHE INC., Nutley, NJ (US)

( * ) Notice: Subject to any disclaimer, the term of this patent is extended or adjusted under 35 U.S.C. 154(b) by 0 days.

(21) Appl. No.: 13/738,649

(22) Filed: Jan. 10, 2013

(65) Prior Publication Data

US 2013/0196965 A1    Aug. 1, 2013

(30) Foreign Application Priority Data

Jan. 11, 2012    (EP) .................................... 12150740

(51) Int. Cl.

| | | |
|---|---|---|
| C07D 413/04 | (2006.01) | |
| C07D 413/06 | (2006.01) | |
| C07D 413/10 | (2006.01) | |
| C07D 413/12 | (2006.01) | |
| C07D 273/01 | (2006.01) | |
| C07D 269/00 | (2006.01) | |
| C07D 498/06 | (2006.01) | |
| C07D 515/06 | (2006.01) | |
| C07D 273/02 | (2006.01) | |
| C07D 498/08 | (2006.01) | |
| C07D 498/18 | (2006.01) | |
| C07D 498/22 | (2006.01) | |
| C07D 515/08 | (2006.01) | |
| C07D 515/22 | (2006.01) | |

(52) U.S. Cl.
CPC ............ *C07D 273/01* (2013.01); *C07D 269/00* (2013.01); *C07D 273/02* (2013.01); *C07D 413/10* (2013.01); *C07D 498/06* (2013.01); *C07D 498/08* (2013.01); *C07D 498/18* (2013.01); *C07D 498/22* (2013.01); *C07D 515/06* (2013.01); *C07D 515/08* (2013.01); *C07D 515/22* (2013.01)

(58) Field of Classification Search
CPC .. C07D 413/04; C07D 413/06; C07D 413/10; C07D 413/12
See application file for complete search history.

(56) References Cited

FOREIGN PATENT DOCUMENTS

| WO | 00/59929 | 10/2000 |
| WO | 2007/077004 A1 | 7/2007 |
| WO | 2009/001129 A1 | 12/2008 |

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784.*
Sheridan (J. Chem. Inf. Comput. Sci., 2002, vol. 42, pp. 103-108).*

* cited by examiner

*Primary Examiner* — Jeffrey S Lundgren
*Assistant Examiner* — Chris Simmons
(74) *Attorney, Agent, or Firm* — Genentech, Inc.

(57) ABSTRACT

The invention relates to a compound of formula (I)

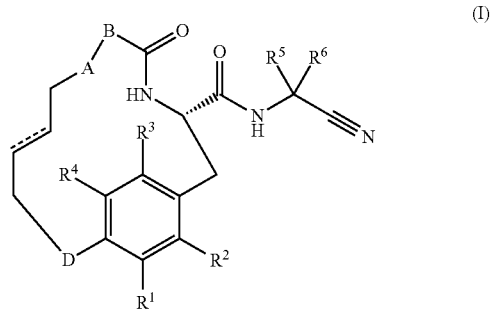

(I)

wherein A, B, D and $R^1$ to $R^6$ are defined as in the description and in the claims. The compound of formula (I) can be used as a medicament.

11 Claims, No Drawings

CYCLIC AMIDES

CROSS REFERENCE TO RELATED APPLICATIONS

This application claims priority under 35 USC §119 to EP Application No. 12150740.4 filed on Jan. 11, 2012, the disclosure of which is incorporated herein by reference.

FIELD OF THE INVENTION

The present invention relates to organic compounds useful for therapy and/or prophylaxis in a mammal, and in particular to compounds that are preferential inhibitors of the cysteine protease cathepsin, in particular of the cysteine protease cathepsin L.

BACKGROUND OF THE INVENTION

Mammalian cathepsins are cysteine-type proteases involved in key steps of biological and pathological events. Cathepsins are considered tractable drug targets as it is feasible to inhibit their enzymatic activity with small molecules and are therefore of interest to the pharmaceutical industry. Cathepsins are mainly located in the acidic compartments of the cells, like lysosomes and endosomes. In addition, cathepsins are secreted and work in the extracellular space, as well as in the cell cytoplasm and in the nucleus. In particular cathepsin L has a broad cellular distribution in all these compartments. By the use of alternative translation start sides downstream from the first AUG, alternative Cat L forms are generated devoid of the leader sequence. The truncated Cat L proteins are directed to the cytoplasm and the nucleus. Based on its cellular location, Cat L performs different cell biological activities.

Data from LDLrec (low density lipoprotein receptor) and Cat L deficient mice highlight the role of cathepsin L in atherosclerosis, as these mice show a reduced atherosclerotic phenotype (Kitamoto et al., Circulation 2007, 115:2065-75). Likewise, Cat L deficient mice have less severe lesions in the elastase induced model of abdominal aortic aneurism (Sun et al., Arterioscler Thromb Vasc Biol. 2011, 31:2500-8). Cat L contributes to vascular lesion formation by promoting inflammatory cell accumulation, angiogenesis, and protease expression. It is involved in matrix degradation, e.g. elastin and collagen, as a secreted protease, in autophagic cell death as cytoplasmic proteases (Mahmood et al., J. Biol. Chem. 2011, 286:28858-66) or by processing transcription factors like Cux-1 as a nuclear protease (Goulet et al., Mol. Cell. 2004, 14:207-19; Goulet et al., Biol. Chem. 2006, 387:1285-93). Human vascular disease samples from atherosclerotic vasculature or AAA (abdominal aortic aneurism) patients show strong upregulation of Cat L in diseases tissue (Liu et al., Atherosclerosis 2006, 184:302-11).

Cytoplasmic variants of Cat L seem to play a key role in proteinuric diseases. The podocyte is a key cell type maintaining the barrier function of the glomeruli in the kidney. Proinflammatory signals like LPS (lipopolysaccharide) induce Cat L expression. Cytoplasmic Cat L cleaves proteins that regulate the placticity of the cytoskeleton: dynamin and synaptopodin. Cat L deficient mice show reduced proteinurea in models of acute proteinurea (Reiser et al., J. Clin. Invest. 2010, 120:3421-31; Yaddanapudi et al., J. Clin. Invest. 2011, 121:3965-80).

Cat L deficient mice show a reduced metabolic phenotype when challenged towards different diabetic condition. Part of the mechanism is the cleavage of the insulin-receptor on skeletal muscle cells (Yang et al., Nat. Cell. Biol. 2007, 9:970-7), but matrix degradation as well as cleavage of the Cux-1 and its role in leptin signaling also contribute to the metabolic functions of Cat L (Stratigopoulos et al., J. Biol. Chem. 2011, 286:2155-70).

Cat L has also been shown to be upregulated in a variety of cancers ranging from breast, lung, gastric, colon to melanomas and gliomas. The cellular functions of Cat L in mediating apoptosis, lysosomal recyling, and cell invasion, make inhibition of Cat L in cancer an attractive target. The decrease of cell-cell adhesion by Cat L can partly be explained by cleavage of E-cadherin (Gocheva et al., Genes Dev. 2006, 20:543-56). The cleavage of extracellular matrix can also release growth factors from the matrix to interact with cell surface receptors.

SUMMARY OF THE INVENTION

The invention relates in particular to a compound of formula (I)

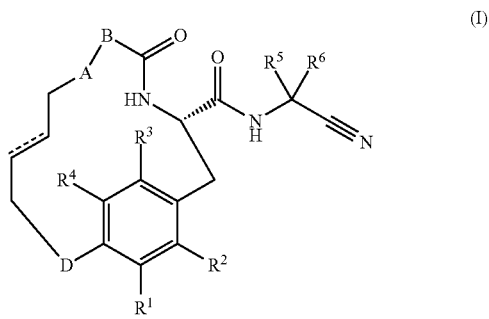

wherein
A is —O—, —S—, —CH$_2$—, —NH— or —SO$_2$—;
B is a five to twelve membered carbocyclic ring or a five to twelve membered heterocyclic ring, wherein the ring is optionally substituted with one or two substituents independently selected from halogen, alkyl, alkoxy, haloalkyl, haloalkoxy, cycloalkyl, cycloalkylalkoxy, sulfonyl, sulfanyl, cycloalkylsulfonyl, cycloalkylsulfanyl, alkoxycarbonylazetidinyl, cyano, azetidinyl or alkylsulfanyl;
D is —O—, —S—, —CH$_2$—, —NH— or —SO$_2$—;
one of R$^1$, R$^2$, R$^3$ and R$^4$ is hydrogen and the other ones are independently selected from hydrogen, halogen, alkyl, alkoxy, haloalkoxy, cycloalkyl and phenyl;
R$^5$ and R$^6$ are independently selected from and hydrogen, alkyl, haloalkyl, cycloalkyl, phenyl and phenylalkyl;
or R$^5$ and R$^6$ together with the carbon atom to which they are attached form cycloalkyl, pyrrolidinyl or piperidinyl; and
is a carbon-carbon single bond or a carbon-carbon double bond;
or a pharmaceutically acceptable salt or ester thereof.

The compounds of the invention are preferential inhibitors of the cysteine protease Cathepsin (Cat), in particular Cathepsin L and are therefore useful to treat metabolic diseases like diabetes and its complications, e.g. diabetic retinopathy and diabetic nephropathy and vascular diseases like atherosclerosis, abdominal aortic aneurysm, peripheral arterial disease, reduction of cardiovascular events in chronic kidney disease and diabetic nephropathy and furthermore cancer, pancreatitis and inflammatory disorders.

DETAILED DESCRIPTION OF THE INVENTION

In the present description the term "alkyl", alone or in combination, signifies a straight-chain or branched-chain alkyl group with 1 to 8 carbon atoms, in particular a straight or branched-chain alkyl group with 1 to 6 carbon atoms and particularly a straight or branched-chain alkyl group with 1 to 4 carbon atoms. Examples of straight-chain and branched C1-C8 alkyl groups are methyl, ethyl, propyl, isopropyl, butyl, isobutyl, tert.-butyl, the isomeric pentyls, the isomeric hexyls, the isomeric heptyls and the isomeric octyls, in particular methyl, ethyl, propyl, isopropyl, isobutyl and tert.-butyl, more particularly methyl.

The term "cycloalkyl", alone or in combination, signifies a cycloalkyl ring with 3 to 8 carbon atoms and particularly a cycloalkyl ring with 3 to 6 carbon atoms. Examples of C3-C8 cycloalkyl are cyclopropyl, cyclobutyl, cyclopentyl, cyclohexyl, cycloheptyl and cyclooctyl. Particular cycloalkyl are cyclopropyl, cyclobutyl, cyclopentyl and cyclohexyl. Cyclopropyl is a particular cycloalkyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, in particular methoxy, ethoxy, propoxy and isopropoxy, more particularly methoxy.

The term "cycloalkyloxy", alone or in combination, signifies a group of the formula cycloalkyl-O— in which the term "cycloalkyl" has the previously given significance, such as cyclobutyloxy, cyclopentyloxy or cyclohexyloxy.

The term "oxy", alone or in combination, signifies the —O— group.

The term "halogen" or "halo", alone or in combination, signifies fluorine, chlorine, bromine or iodine.

The terms "haloalkyl", "halocycloalkyl" and "haloalkoxy", alone or in combination, denote an alkyl group, a cycloalkyl group and an alkoxy group substituted with at least one halogen, in particular substituted with one to five halogens, particularly one to three halogens. Fluoroalkyl is an alkyl group substituted with at least one fluorine atom, particularly substituted with one to five fluorine atoms, more particularly one to three halogens. A particular haloalkyl is trifluoromethyl.

The term sulfanyl, alone or in combination, means —S—.

The term sulfonyl, alone or in combination, means —$SO_2$—.

The term "five to twelve membered carbocyclic ring", alone or in combination, means a carbocyclic ring containing five to twelve ring carbon atoms, which can be saturated or unsaturated, and which is linked to the rest of the compound of formula (I) through two ring atoms. Examples of five to twelve membered carbocyclic rings are phenyl, naphthalenyl, 1,2,3,4-tetrahydronaphthalenyl, bicyclo[4.2.0]octa-1(6),2,4-trienyl, indanyl and 6,7,8,9-tetrahydro-5H-benzocycloheptenyl, in particular phenyl and 1,2,3,4-tetrahydronaphthalenyl, and more particularly phenyl.

The term "five to twelve membered heterocyclic ring", alone or in combination, means a carbocyclic ring containing five to twelve ring carbon atoms, which can be saturated or unsaturated, which contains one to three heteroatoms selected from N, O or S and is linked to the rest of the compound of formula (I) through two ring atoms. Examples of five to twelve membered heterocyclic ring are pyrrolidinyl, pyridinyl, pyrimidinyl, pyridazinyl, pyrazinyl, pyrazolyl, imidazolyl, 1,2,3-triazolyl, 1,2,4-triazolyl, tetrazolyl, indolyl, benzimidazolyl, benztriazolyl, pyrrolopyridinyl, pyrazolopyridinyl, triazolopyridinyl and imidazolopyridinyl, in particular pyrrolidinyl, pyridinyl and pyrimidinyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, in particular, hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

If one of the starting materials or compounds of formula (I) contains one or more functional groups which are not stable or are reactive under the reaction conditions of one or more reaction steps, appropriate protecting groups (as described e.g. in "Protective Groups in Organic Chemistry" by T. W. Greene and P. G. M. Wutts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention relates in particular to a compound of formula (I)

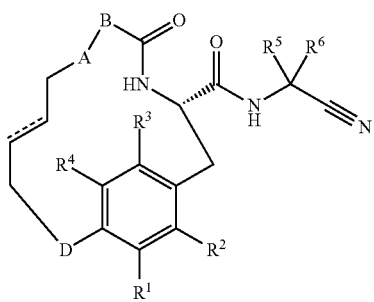
(I)

wherein:
A is —O—, —S—, —CH₂—, —NH— or —SO₂—;
B is a five to twelve membered carbocyclic ring or a five to twelve membered heterocyclic ring, wherein the ring is optionally substituted with one or two substituents independently selected from halogen, alkyl, alkoxy, haloalkyl, haloalkoxy, cycloalkyl, cycloalkylalkoxy, sulfonyl, sulfanyl, cycloalkylsulfonyl and cycloalkylsulfanyl;
D is —O—, —S—, —CH₂—, —NH— or —SO₂—;
one of $R^1$, $R^2$, $R^3$ and $R^4$ is hydrogen and the other ones are independently selected from hydrogen, halogen, alkyl, alkoxy, haloalkoxy, cycloalkyl and phenyl;
$R^5$ and $R^6$ are independently selected from and hydrogen, alkyl, haloalkyl, cycloalkyl, phenyl and phenylalkyl;
or $R^5$ and $R^6$ together with the carbon atom to which they are attached form cycloalkyl, pyrrolidinyl or piperidinyl; and is a carbon-carbon single bond or a carbon-carbon double bond;
or a pharmaceutically acceptable salt or ester thereof.

The invention relates in particular to the following:
A compound of formula (I), wherein A is —O—, —S—, —CH₂— or —NH—;
A compound according of formula (I), wherein B is phenyl, substituted phenyl, pyrrolidinyl, substituted pyrrolidinyl, pyridinyl, substituted pyridinyl, pyrimidinyl, substituted pyrimidinyl, 1,2,3,4-tetrahydronaphtalenyl, bicyclo[4.2.0]octa-1(6),2,4-trienyl, indanyl or 6,7,8,9-tetrahydro-5H-benzocycloheptenyl, wherein substituted phenyl is phenyl substituted with one or two substituents selected from halogen, alkyl, cycloalkyl, alkoxy, haloalkyl, haloalkoxy, azetidinyl, alkylsulfanyl and cyano, wherein substituted pyrrolidinyl is pyrrolidinyl substituted with one or two substituents independently selected from halogen, alkyl, alkoxy, haloalkoxy, cycloalkyl, alkylsulfanyl, alkylsulfonyl, cycloalkylsulfanyl and cycloalkylsulfonyl, wherein substituted pyridinyl is pyridinyl substituted with halogen, alkyl, cycloalkyl, alkoxy or haloalkoxy, and wherein substituted pyrimidinyl is pyrimidinyl substituted with halogen, alkyl, cycloalkyl, alkoxy or haloalkoxy;
A compound of formula (I), wherein B is phenyl, halophenyl, pyrrolidinyl, halopyrrolidinyl, alkylpyrrolidinyl, alkoxyphenyl, alkylpyrridinyl, haloalkylphenyl, tetrahydronaphtyl, azetidinylphenyl, cyanophenyl or alkylsulfanylphenyl;
A compound of formula (I), wherein B is phenyl, bromophenyl, chlorophenyl, difluorophenyl, methoxyphenyl or methylpyridinyl, trifluoromethylphenyl, azetidinylphenyl, cyanophenyl or methylsulfanylphenyl;
A compound of formula (I), wherein B is phenyl, substituted phenyl, pyrrolidinyl, substituted pyrrolidinyl, pyridinyl, substituted pyridinyl, pyrimidinyl, substituted pyrimidinyl, 1,2,3,4-tetrahydronaphtalenyl, bicyclo[4.2.0]octa-1(6),2,4-trienyl, indanyl or 6,7,8,9-tetrahydro-5H-benzocycloheptenyl, wherein substituted phenyl is phenyl substituted with one or two substituents selected from halogen, alkyl, cycloalkyl, alkoxy and haloalkoxy, wherein substituted pyrrolidinyl is pyrrolidinyl substituted with one or two substituents independently selected from halogen, alkyl, alkoxy, haloalkoxy, cycloalkyl, alkylsulfanyl, alkylsulfonyl, cycloalkylsulfanyl and cycloalkylsulfonyl, wherein substituted pyridinyl is pyridinyl substituted with halogen, alkyl, cycloalkyl, alkoxy or haloalkoxy, and wherein substituted pyrimidinyl is pyrimidinyl substituted with halogen, alkyl, cycloalkyl, alkoxy or haloalkoxy;
A compound of formula (I), wherein B is phenyl, halophenyl, pyrrolidinyl, halopyrrolidinyl, alkylpyrrolidinyl, alkoxyphenyl, alkylpyrridinyl, haloalkylphenyl or tetrahydronaphtyl;
A compound of formula (I), wherein B is phenyl, bromophenyl, chlorophenyl, methoxyphenyl or methylpyridinyl;
A compound of formula (I), wherein D is —O—;
A compound of formula (I), wherein one of $R^1$ and $R^4$ is hydrogen and the other one is halogen;
A compound of formula (I), wherein one of $R^1$ and $R^4$ is hydrogen and the other one is bromo, chloro or iodo;
A compound of formula (I), wherein $R^2$ and $R^3$ are both hydrogen the same time;
A compound of formula (I), wherein $R^5$ and $R^6$ together with the carbon atom to which they are attached form cycloalkyl; and
A compound of formula (I), wherein $R^5$ and $R^6$ together with the carbon atom to which they are attached form cyclopropyl.

The invention further relates to a compound of formula (I) selected from:
(E)-(S)-5-Oxo-12,17-dioxa-4-aza-tricyclo[16.2.2.0*6,11*]docosa-1(21),6(11),7,9,14,18(22),19-heptaene-3-carboxylic acid (1-cyano-cyclopropyl)-amide;
(E)-(S)-5-Oxo-11,16-dioxa-4-aza-tricyclo[15.2.2.1*6,10*]docosa-1(20),6,8,10(22),13,17(21),18-heptaene-3-carboxylic acid (1-cyano-cyclopropyl)-amide;
(E)-(S)-5-Oxo-17-oxa-4-aza-tricyclo[16.2.2.0*6,11*]docosa-1(21),6,8,10,14,18(22),19-heptaene-3-carboxylic acid (1-cyano-cyclopropyl)-amide;
(E)-(S)-19-Chloro-5-oxo-12,17-dioxa-4-aza-tricyclo[16.2.2.0*6,11*]docosa-1(21),6(11),7,9,14,18(22),19-heptaene-3-carboxylic acid (1-cyano-cyclopropyl)-amide;
(E)-(S)-19-Chloro-5-oxo-17-oxa-4-aza-tricyclo[16.2.2.0*6,11*]docosa-1(21),6,8,10,14,18(22),19-heptaene-3-carboxylic acid (1-cyano-cyclopropyl)-amide;
(E)-(S)-18-Chloro-5-oxo-11,16-dioxa-4-aza-tricyclo[15.2.2.1*6,10*]docosa-1(20),6,8,10(22),13,17(21),18-heptaene-3-carboxylic acid (1-cyano-cyclopropyl)-amide;
(S)-19-Chloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;
(E)-(S)-8-Bromo-19-chloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;
(S)-8-Bromo-19-chloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;
(E)-(S)-8,19-Dichloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-8,19-Dichloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E)-(S)-18-Chloro-5-oxo-16-oxa-4,10-diaza-tricyclo[15.2.2.0*6,10*]henicosa-1(20),13,17(21),18-tetraene-3-carboxylic acid (1-cyano-cyclopropyl)-amide;

(E)-(3S,8S)-18-Chloro-8-fluoro-5-oxo-16-oxa-4,10-diaza-tricyclo[15.2.2.0*6,10*]henicosa-1(20),13,17(21),18-tetraene-3-carboxylic acid (1-cyano-cyclopropyl)-amide;

(E)-(S)-18-Chloro-8,8-difluoro-5-oxo-16-oxa-4,10-diaza-tricyclo[15.2.2.0*6,10*]henicosa-1(20),13,17(21),18-tetraene-3-carboxylic acid (1-cyano-cyclopropyl)-amide;

(E)-(S)-18-Chloro-8,8-dimethyl-5-oxo-16-oxa-4,10-diaza-tricyclo[15.2.2.0*6,10*]henicosa-1(20),13,17(21),18-tetraene-3-carboxylic acid (1-cyano-cyclopropyl)-amide;

(E)-(S)-19-Chloro-8-methoxy-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-19-Chloro-8-methoxy-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E)-(S)-19-Chloro-9-methoxy-5-oxo-17-oxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-9-methyl-5-oxo-17-oxa-12-thia-4,10-diaza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-5-oxo-9-trifluoromethyl-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-5-oxo-17-oxa-4,12-diaza-tricyclo[16.2.2.0*6,11*]docosa-1(21),6,8,10,14,18(22),19-heptaene-3-carboxylic acid (1-cyano-cyclopropyl)-amide;

(S)-19-Chloro-9-methoxy-5-oxo-17-oxa-4-aza-tricyclo[16.2.2.0*6,11*]docosa-1(21),6,8,10,18(22),19-hexaene-3-carboxylic acid (1-cyano-cyclopropyl)-amide;

(S)-19-Chloro-5-oxo-9-trifluoromethyl-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E)-(S)-19-Iodo-5-oxo-12,17-dioxa-4-aza-tricyclo[16.2.2.*6,11*]docosa-1(21),6,8,10,14,18(22),19-heptaene-3-carboxylic acid (1-cyano-cyclopropyl)-amide;

(E)-(S)-19-Iodo-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide, stereoaxis R;

(E)-(S)-19-Iodo-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide, stereoaxis S;

(3E,12S)-22-chloro-N-(1-cyanocyclopropyl)-14-oxo-2,5,11,12,13,14,16,17,18,19-decahydro-7,10-ethenonaphtho[2,3-b][1,12,5]dioxazacyclohexadecine-12-carboxamide;

(E)-(S)-8-Chloro-19-iodo-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(12S)-22-chloro-N-(1-cyanocyclopropyl)-14-oxo-2,3,4,5,11,12,13,14,16,17,18,19-dodecahydro-7,10-ethenonaphtho[2,3-b][1,12,5]dioxazacyclohexadecine-12-carboxamide;

(S)-19-Iodo-5-oxo-12,17-dioxa-4-aza-tricyclo[16.2.2.0*6,11*]docosa-1(21),6(11),7,9,18(22),19-hexaene-3-carboxylic acid (1-cyano-cyclopropyl)-amide;

(S)-8-Chloro-19-iodo-5-oxo-12,17-dioxa-4-aza-tricyclo[16.2.2.0*6,11*]docosa-1(21),6(11),7,9,18(22),19-hexaene-3-carboxylic acid (1-cyano-cyclopropyl)-amide (E)-(S)-19-Chloro-8-fluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-9,19-Dichloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-5-oxo-8-trifluoromethyl-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-19-Chloro-8-fluoro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(S)-9,19-Dichloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(S)-19-Chloro-5-oxo-8-trifluoromethyl-12,17-dioxa-4-aza-tricyclo[16.2.2.0*6,11*]docosa-1(21),6,8,10,18(22),19-hexaene-3-carboxylic acid (1-cyano-cyclopropyl)-amide; and (E)-(S)-8-Bromo-19-chloro-5-oxo-17-oxa-4,12-diaza-tricyclo[16.2.2.0*6,11*]docosa-1(21),6,8,10,14,18(22),19-heptaene-3-carboxylic acid (1-cyano-cyclopropyl)-amide.

The invention further relates to a compound of formula (I) selected from:

3-[(E)-(S)-19-Chloro-3-(1-cyano-cyclopropylcarbamoyl)-5-oxo-12,17-dioxa-4-aza-tricyclo[16.2.2.0*6,11*]docosa-1(21),6,8,10,14,18(22),19-heptaen-8-yl]-azetidine-1-carboxylic acid tert-butyl ester;

(E)-(S)-19-Chloro-8-cyano-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-8-Azetidin-3-yl-19-chloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

3-[(S)-19-Chloro-3-(1-cyano-cyclopropylcarbamoyl)-5-oxo-12,17-dioxa-4-aza-tricyclo[16.2.2.0*6,11]docosa-1(21),6,8,10,18(22),19-hexaen-8-yl]-azetidine-1-carboxylic acid tert-butyl ester;

(S)-8-Azetidin-3-yl-19-chloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E-Z)—(S)-19-Chloro-8,10-difluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-7,8-difluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(Z)—(S)-19-Chloro-7,8-difluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-8-methylsulfanyl-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-10,19-Dichloro-8-fluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-19-Chloro-8-cyano-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(S)-19-Chloro-7,8-difluoro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide; and (S)-19-Chloro-8-methylsulfanyl-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide.

The invention also relates to a compound of formula (I) selected from:

(E)-(S)-19-Chloro-5-oxo-12,17-dioxa-4-aza-tricyclo[16.2.2.0*6,11*]docosa-1(21),6(11),7,9,14,18(22),19-heptaene-3-carboxylic acid (1-cyano-cyclopropyl)-amide;

(E)-(S)-19-Chloro-5-oxo-17-oxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-18-Chloro-5-oxo-11,16-dioxa-4-aza-tricyclo[15.2.2.1*6,10*]docosa-1(20),6,8,10(22),13,17(21),18-heptaene-3-carboxylic acid (1-cyano-cyclopropyl)-amide;

(E)-(S)-8-Bromo-19-chloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-8-Bromo-19-chloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E)-(S)-8,19-Dichloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-8,19-Dichloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E)-(S)-19-Chloro-8-methoxy-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-19-Chloro-8-methoxy-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E)-(S)-19-Chloro-9-methyl-5-oxo-17-oxa-12-thia-4,10-diaza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-5-oxo-8-trifluoromethyl-12,17-dioxa-4-aza-tricyclo[16.2.2.0*6,11*]docosa-1(21),6,8,10,14,18(22),19-heptaene-3-carboxylic acid (1-cyano-cyclopropyl)-amide; and (S)-19-Chloro-5-oxo-8-trifluoromethyl-12,17-dioxa-4-aza-tricyclo[16.2.2.0*6,11*]docosa-1(21),6,8,10,18(22),19-hexaene-3-carboxylic acid (1-cyano-cyclopropyl)-amide.

The invention also relates in particular to a compound of formula (I) selected from:

(E)-(S)-19-Chloro-5-oxo-8-trifluoromethyl-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-19-Chloro-5-oxo-8-trifluoromethyl-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E)-(S)-8-Azetidin-3-yl-19-chloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-8-Azetidin-3-yl-19-chloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E-Z)—(S)-19-Chloro-8,10-difluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-7,8-difluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-8-methylsulfanyl-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-19-Chloro-8-cyano-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(S)-19-Chloro-7,8-difluoro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide; and (S)-19-Chloro-8-methylsulfanyl-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide.

The compounds of formula (I) can be prepared according to procedures known in the art to the skilled person, and in particular according to the reactions described below.

Scheme 1

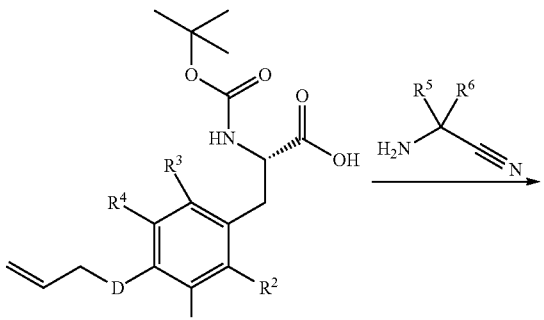

-continued

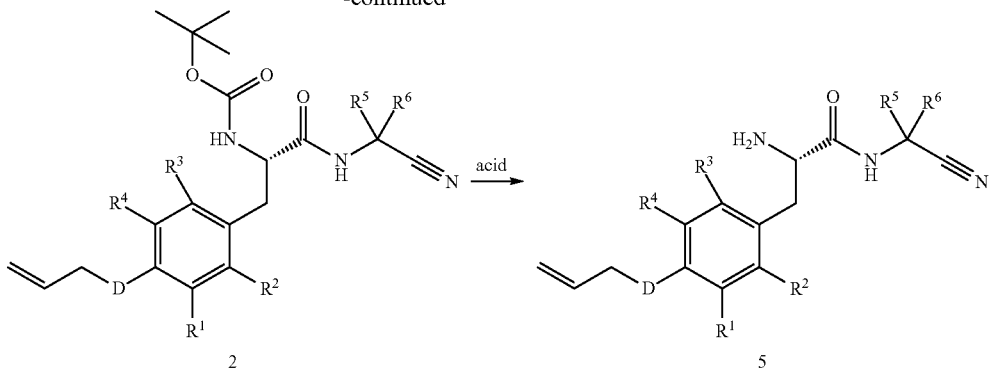

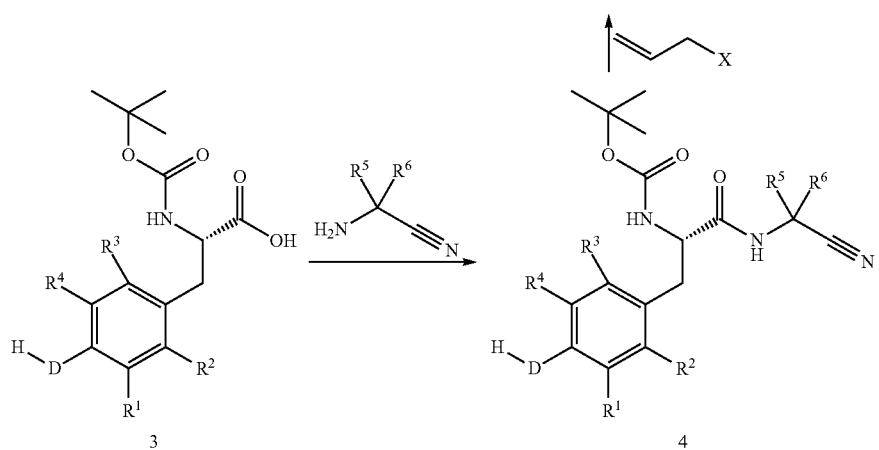

R$^{1-4}$ and D are as defined above; X is a leaving group such as Cl, Br, I, OH, mesylate, tosylate, nosylate, brosylate or triflate.

A protected amino acid derivative such as 1 or 3 is reacted with an aminoacetonitrile derivative in presence of one of the various amide coupling reagents such as BOP—Cl, TBTU, BOP, PyBop, HATU, EDCI/HOBT, DIC/HOBT, DCC/HOBT, etc. to yield corresponding amides 2 or 4. Amide 4 is transferred into amide 2 by reaction of
X—CH$_2$—CH=CH$_2$ with 4 in the presence of a base or via a Mitsunobu reaction in the presence of a phosphine derivative such as PPh$_3$ etc. Amine 5 is obtained by reaction of amide 2 with an appropriate acid such as TFA, formic acid, HCl in dioxane, etc. and subsequent basic extraction.

Scheme 2

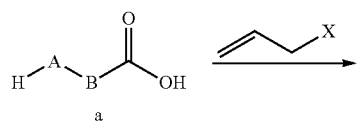

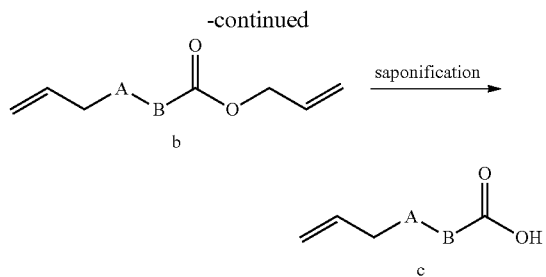

A and B are as defined above; X is a leaving group such as Cl, Br, I, OH, mesylate, tosylate, nosylate, brosylate or triflate.

Compound b is obtained by reaction of the carboxylic acid a with X—CH$_2$—CH=CH$_2$ in the presence of a base or via a Mitsunobu reaction in the presence of a phosphine derivative such as PPh$_3$ etc. The ester b is then subsequently saponified by treating b with a base such as NaOH, KOH, LiOH, etc to yield the final building blocks c.

Scheme 3
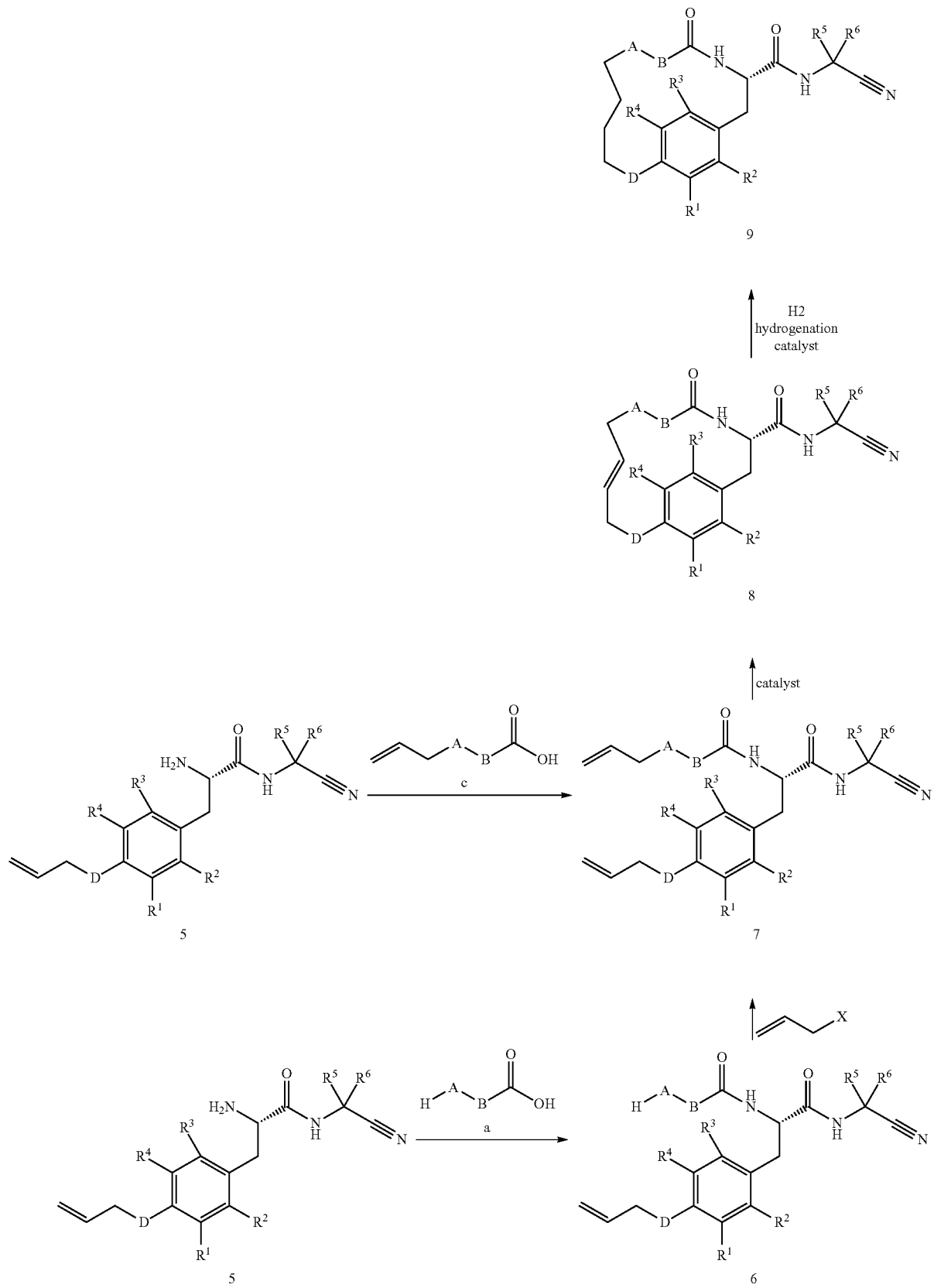

A, B, $R^{1-4}$ and D are as defined above; X is a leaving group such as Cl, Br, I, OH, mesylate, tosylate, nosylate, brosylate or triflate; or X is A-Y, wherein Y is the leaving group as defined above. In the latter case A is not present in carboxylic acid a used for the reaction from 5 to 6.

Amine 5 is reacted with the carboxylic acid derivatives a or c to amides 6 or 7 in presence of one of the various amide coupling reagents such as BOP—Cl, TBTU, BOP, PyBop, HATU, EDCI/HOBT, DIC/HOBT; DCC/HOBT, etc. Amide 6 is transferred into amide 7 by reaction of X—$CH_2$—CH=$CH_2$ with 6 in the presence of a base or via a Mitsunobu reaction in the presence of a phosphine derivative such as $PPh_3$ etc. The macrocycle 8 is obtained by ring closing metathesis of 7 using one of the catalysts known in the art (e.g. Grubbs I, Grubbs II, Grubbs Hoveyda I or II, etc.) with or without (Lewis) acid catalysis. The macrocycle 9 is obtained by a catalytic hydrogenation of compound 8 using hydrogen under atmospheric or high pressure and one of various hydrogenation catalysts known in the art (e.g. Pd/C; Raney nickel, $PtO_2$, etc.)

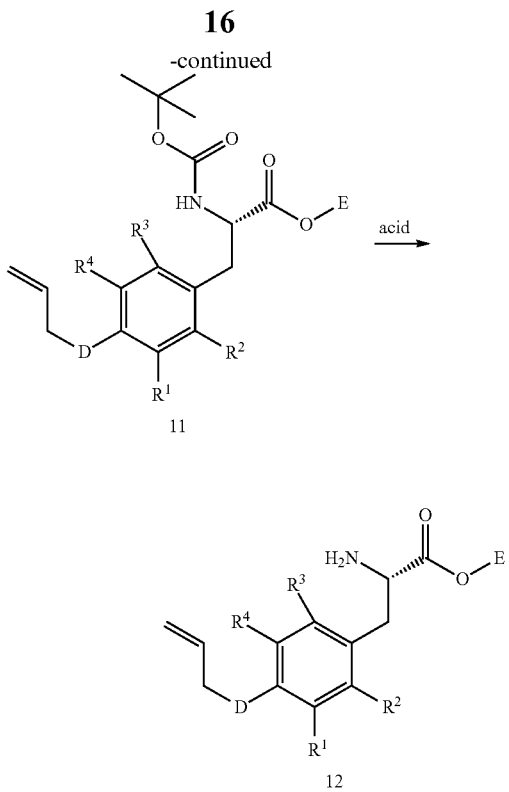

Scheme 4

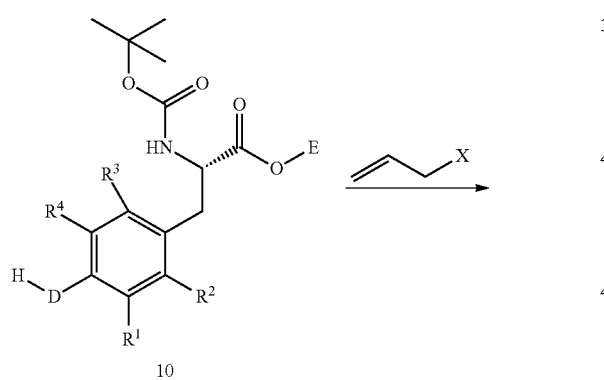

$R^{1-2}$ and D are as defined above; X is a leaving group such as Cl, Br, I, OH, mesylate, tosylate, nosylate, brosylate or triflate; E is methyl, ethyl, propyl, benzyl or isopropyl.

The orthogonally protected amino acid derivative 10 is treated with X—$CH_2$—CH=$CH_2$ in the presence of a base or via a Mitsunobu reaction in the presence of a phosphine derivative such as $PPh_3$ etc. to yield compound II. Cleavage of the amino protecting group by an appropriate acid such as TFA, formic acid, HCl in dioxane, etc. and subsequent basic extraction yields the free amine 12.

Scheme 5

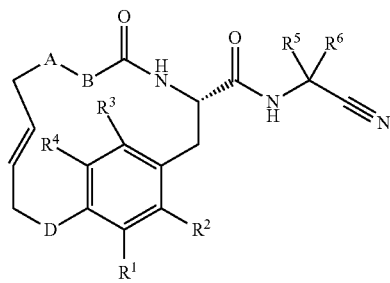

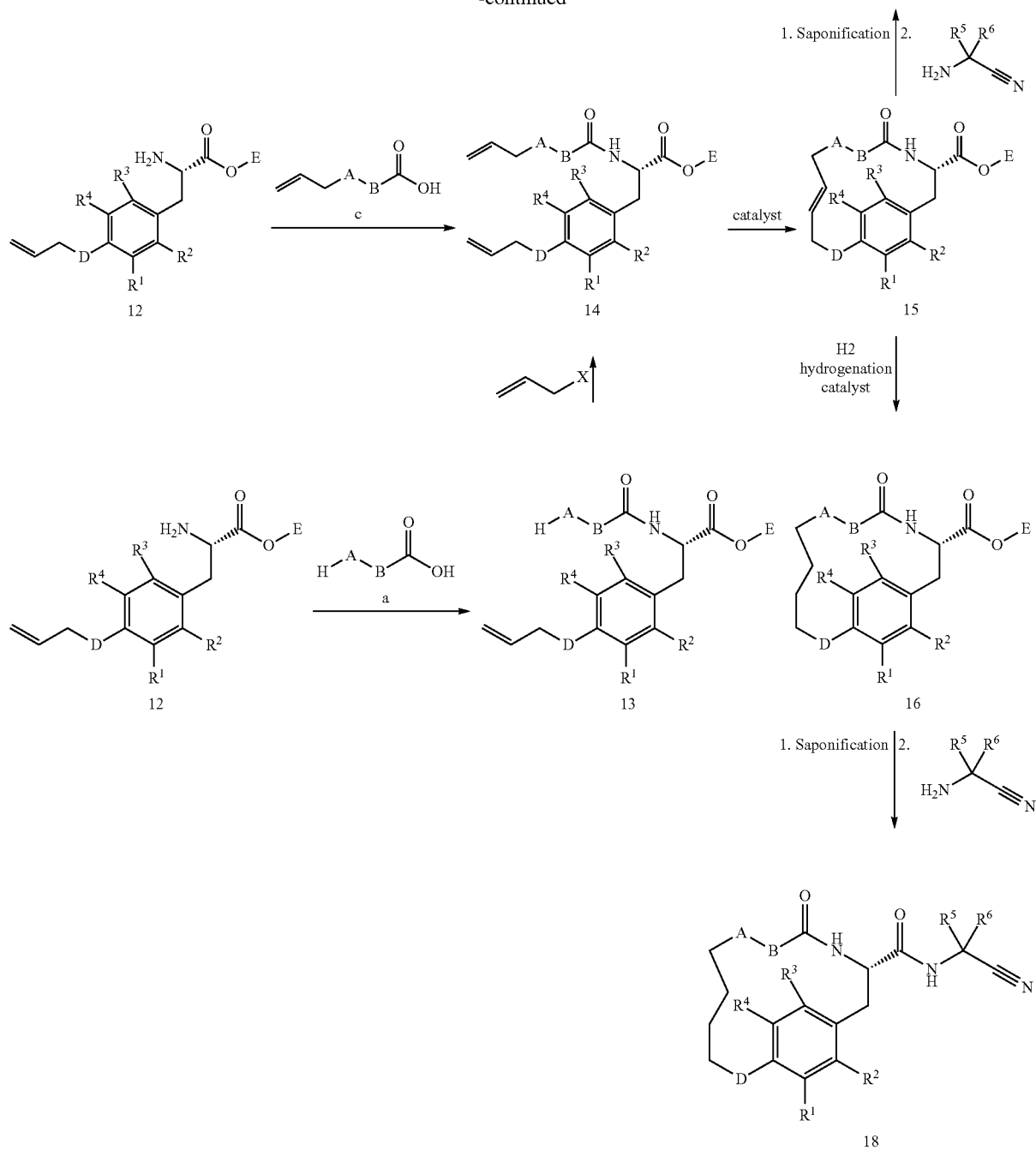

A, B, $R^{1-4}$ and D are as defined above; X is a leaving group such as Cl, Br, I, OH, mesylate, tosylate, nosylate, brosylate or triflate; or X is A-Y, wherein Y is the leaving group as defined above. In the latter case A is not present in carboxylic acid a used for the reaction from 12 to 13. E is methyl, ethyl, propyl, benzyl or isopropyl.

Amine 12 is reacted with the carboxylic acid derivatives a or c to amides 13 or 14 in presence of one of the various amide coupling reagents such as BOP—Cl, TBTU, BOP, PyBop, HATU, EDCI/HOBT, DIC/HOBT, DCC/HOBT, etc. Amide 13 is transferred into amide 14 by reaction of X—CH$_2$—CH=CH$_2$ with 13 in the presence of a base or via a Mitsunobu reaction in the presence of a phosphine derivative such as PPh$_3$ etc. The macrocycle 15 is obtained by ring closing metathesis of 14 using one of the catalysts known in the art (e.g. Grubbs I, Grubbs II, Grubbs Hoveyda I or II, etc.) with or without (Lewis) acid catalysis. The macrocycle 16 is obtained by a catalytic hydrogenation of compound 15 using hydrogen under atmospheric or high pressure and one of the various hydrogenation catalysts known in the art (e.g. Pd/C; Raney nickel, PtO$_2$, etc.). Both macrocycles 15 or 16 are then saponified using a base such as LiOH, NaOH, KOH, etc to the corresponding carboxylic acids which are then subsequently reacted with aminoacetonitrile derivatives in the presence of one of the various amide coupling reagents such as BOP—Cl, TBTU, BOP, PyBop, HATU, EDCI/HOBT, DIC/HOBT, DCC/HOBT, etc. to the final macrocyclic amides 17 and 18.

Scheme 6

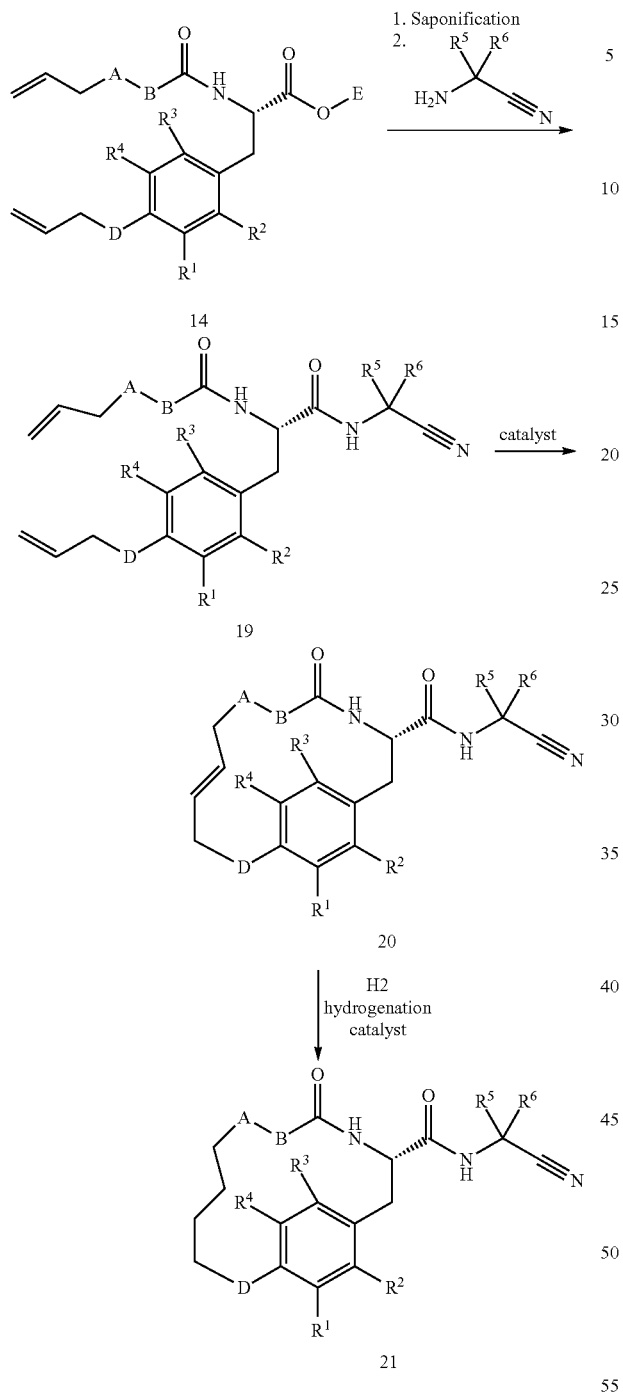

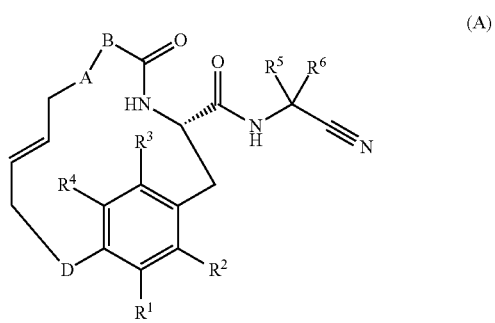

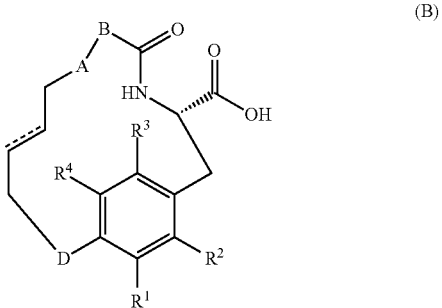

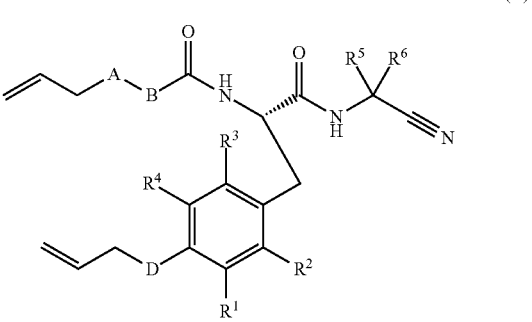

A, B, R$^{1-4}$ and D are as defined above; E is methyl, ethyl, propyl, benzyl or isopropyl.

Compound 14 (see scheme 5) is saponified using a base such as LiOH, NaOH, KOH, etc to the corresponding carboxylic acid which are then subsequently reacted with aminoacetonitrile derivatives in the presence of one of the various amide coupling reagents such as BOP—Cl, TBTU, BOP, PyBop, HATU, EDCI/HOBT, DIC/HOBT; DCC/HOBT, etc. to yield amide 19. The macrocycle 20 is obtained by ring closing metathesis using one of the catalysts known in the art (e.g. Grubbs I, Grubbs II, Grubbs Hoveyda I or II, etc.) with or without (Lewis) acid catalysis. The macrocycle 21 is obtained by a catalytic hydrogenation of compound 20 using hydrogen under atmospheric or high pressure and one of the various hydrogenation catalysts known in the art (e.g. Pd/C; Raney nickel, PtO$_2$, etc.)

The invention further relates to a process for the preparation of a compound of formula (I) comprising on of the following steps:

(a) the reaction of a compound of formula (A)

in the presence of hydrogen and a hydrogenation catalyst;

(b) the reaction of a compound of formula (B)

(c) the reaction of a compound of formula (C)

in the presence of a ring closing metathesis catalyst;

wherein R$^1$ to R$^6$, A, B, D and ---- are as defined above.

In step (a), examples of hydrogenation catalysts are Pd/C, Raney Nickel, PtO$_2$, Wilkinson catalyst, Crabtree's catalyst and other Fe, Ru or Ir based catalysts, well-known to the skilled person.

In step (c), examples of ring closing metathesis catalysts are Grubbs I catalyst (benzylidenbis(tricyclohexylphosphin)

dichlororuthenium), Grubbs II catalyst (benzyliden[1,3-bis (2,4,6-trimethylphenyl)-2-imidazolidinyliden]dichloro-(tricyclohexylphosphin)ruthenium), Grubbs Hoveyda I catalyst (dichloro(o-isopropoxyphenylmethylen)(tricyclohexylphosphin)ruthenium(II)) and Grubbs Hoveyda II catalyst (1,3-bis-(2,4,6-trimethylphenyl)-2-imidazolidinyliden)-dichloro(o-isopropoxyphenylmethylen)ruthenium).

The invention also relates to a compound of formula (I), when manufactured according to a process of the invention.

The invention further relates to:

A compound of formula (I) for use as therapeutically active substance;

A pharmaceutical composition comprising a compound of formula (I) and a therapeutically inert carrier;

The use of a compound of formula (I) for the treatment or prophylaxis of diabetes, diabetic retinopathy, diabetic nephropathy, atherosclerosis, abdominal aortic aneurysm, peripheral arterial disease, chronic kidney disease, diabetic nephropathy, cancer or pancreatitis;

The use of a compound of formula (I) for the preparation of a medicament for the treatment or prophylaxis of diabetes, diabetic retinopathy, diabetic nephropathy, atherosclerosis, abdominal aortic aneurysm, peripheral arterial disease, chronic kidney disease, diabetic nephropathy, cancer or pancreatitis;

A compound of formula (I) for the treatment or prophylaxis of diabetes, diabetic retinopathy, diabetic nephropathy, atherosclerosis, abdominal aortic aneurysm, peripheral arterial disease, chronic kidney disease, diabetic nephropathy, cancer or pancreatitis; and A method for the treatment or prophylaxis of diabetes, diabetic retinopathy, diabetic nephropathy, atherosclerosis, abdominal aortic aneurysm, peripheral arterial disease, chronic kidney disease, diabetic nephropathy, cancer or pancreatitis, which method comprises administering an effective amount of a compound of formula (I) to a patient in need thereof.

Another embodiment of the invention provides pharmaceutical compositions or medicaments containing the compound of the invention and a therapeutically inert carrier, diluent or excipient, as well as methods of using the compounds of the invention to prepare such compositions and medicaments. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterilized. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention will now be illustrated by the following examples which have no limiting character.

EXAMPLES

Abbreviations:
AcOEt: Ethyl acetate;
ACN: Acetonitrile;
BOP: Benzotriazolyl-N-oxy-tris(dimethylamino)-phosphonium hexafluorophosphate;
BOP—Cl: Bis-(2-oxo-3-oxazolidinyl)-phosphinic acid chloride;
CDI: 1,1'-Carbonyldiimidazole;
DCM: Dichloromethane
DIEA: Diisopropyl ethyl amine;
DMF: N,N-Dimethylformamide;
EDCI: N-(3-Dimethylaminopropyl)-N'-ethyl-carbodiimide hydrochloride;
Grubbs I: Benzylidenbis(tricyclohexylphosphin)dichlororuthenium;
Grubbs II: Benzyliden[1,3-bis(2,4,6-trimethylphenyl)-2-imidazolidinyliden]dichloro-(tricyclohexylphosphin)ruthenium;
Grubbs Hoveyda I: Dichloro(o-isopropoxyphenylmethylen)(tricyclohexyl-phosphin)ruthenium(II);
Grubbs Hoveyda II: 1,3-Bis-(2,4,6-trimethylphenyl)-2-imidazolidinyliden)-dichloro(o-isopropoxyphenylmethylen)ruthenium;
HATU: O-(7-azabenzotriazol-1-yl)-1,1,3,3-tetramethyluronium hexafluorophosphate;
HOBT: 1-Hydroxybenzotriazole;
Hunig's Base: Ethyl-diisopropyl-amine;
MeOH: Methanol;
Mes-Cl: Mesyl chloride;
$Na_2SO_4$: Sodium sulfate;

Nos-Cl: 3-Nitrobenzenesulfonyl chloride;

PyBOP: Benzotriazol-1-yl-oxytripyrrolidinephosphonium hexafluorophosphate;

TBTU: O-(Benzotriazol-1-yl)-N,N,N',N'-tetramethyluronium terafluoroborate;

THF: Tetrahydrofurane;

TFA: Trifluoroacetic acid; and

Tos-Cl: Toluene-4-sulfonyl chloride.

Example 1

(E)-(S)-5-Oxo-12,17-dioxa-4-aza-tricyclo[16.2.2.0*6,11*]docosa-1(21),6(11),7,9,14,18(22),19-heptaene-3-carboxylic acid (1-cyano-cyclopropyl)-amide

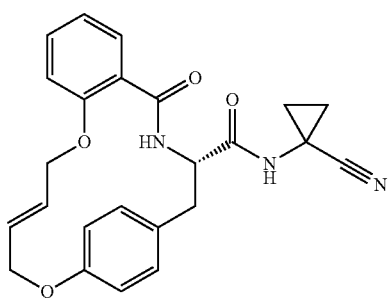 [SMILES: N#CC1(NC(=O)[C@@H]2Cc3ccc(cc3)OC/C=C/COc3ccccc3C(=O)N2)CC1]

A) [(S)-2-(4-Allyloxy-phenyl)-1-(1-cyano-cyclopropylcarbamoyl)-ethyl]-carbamic acid tert-butyl ester

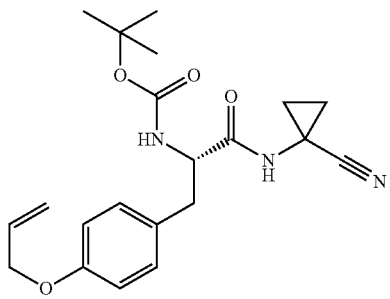 [SMILES: C=CCOc1ccc(C[C@H](NC(=O)OC(C)(C)C)C(=O)NC2(C#N)CC2)cc1]

(S)-3-(4-(allyloxy)phenyl)-2-(tert-butoxycarbonylamino)propanoic acid (5 g, 15.6 mmol, Eq: 1.00) was dissolved in DMF (30 ml). HATU (11.8 g, 31.1 mmol, Eq: 2.00), Hunig's Base (4.02 g, 5.43 ml, 31.1 mmol, Eq: 2.00) and 1-amino-1-cyclopropanecarbonitrile hydrochloride (2.21 g, 18.7 mmol, Eq: 1.20) were added to the above suspension and stirred at 25° C. for 24 h. The reaction mixture was poured into 0.1M HCl (250 mL) and extracted with AcOEt (3×75 mL). The organic layers were dried over $Na_2SO_4$ and concentrated in vacuo. The crude material was dissolved in $CH_2Cl_2$ (10 mL), 2 minutes later it began to precipitate. The suspension was filtered. The filtered solution was purified by flash chromatography (silica gel, 80 g, 0% to 90% AcOEt in heptane) to yield a light yellow solid (3.0 g; 50%). m/z=286.1 [M+H-Boc]$^+$.

B) (S)-3-(4-Allyloxy-phenyl)-2-amino-N-(1-cyano-cyclopropyl)-propionamide

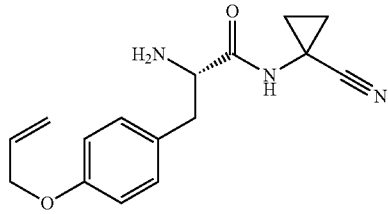 [SMILES: C=CCOc1ccc(C[C@H](N)C(=O)NC2(C#N)CC2)cc1]

Example 1A) (3 g, 7.78 mmol, Eq: 1.00) was dissolved in formic acid (48.0 g, 40 ml, 1.04 mol, Eq: 134) and stirred at 25° C. for 4 h. The reaction mixture was adjusted carefully with icecold aqueous 10% $Na_2CO_3$-solution to pH=8 and extracted with $CH_2Cl_2$. The waterlayer was washed totally 3 times with $CH_2Cl_2$, the combined organic layers were dried over $Na_2SO_4$, filtered and evaporated to dryness to yield a yellow oil (2.0 g; 90%). m/z=286.1 [M+H]$^+$.

C) 2-Allyloxy-N—[(S)-2-(4-allyloxy-phenyl)-1-(1-cyano-cyclopropylcarbamoyl)-ethyl]-benzamide

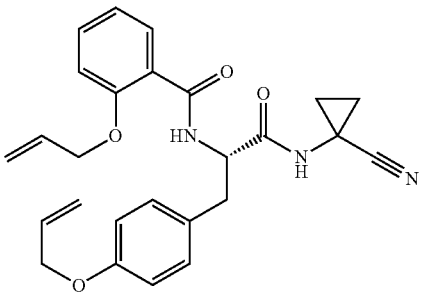 [SMILES: C=CCOc1ccc(C[C@H](NC(=O)c2ccccc2OCC=C)C(=O)NC2(C#N)CC2)cc1]

Example 1B) (150 mg, 526 μmol, Eq: 1.00) was dissolved in DMF (4 mL). HATU (400 mg, 1.05 mmol, Eq: 2.00), Hunig's Base (136 mg, 184 μL, 1.05 mmol, Eq: 2.00) and 2-(allyloxy)benzoic acid (112 mg, 631 μmol, Eq: 1.20) were added to the suspension and stirred at 25° C. for 3 h. The crude material was purified by preparative HPLC to yield an off-white solid (175 mg; 75%). m/z=446.3 [M+H]$^+$.

D) (E)-(S)-5-Oxo-12,17-dioxa-4-aza-tricyclo[16.2.2.0 6,11]docosa-1(21),6(11),7,9,14,18(22),19-heptaene-3-carboxylic acid (1-cyano-cyclopropyl)-amide

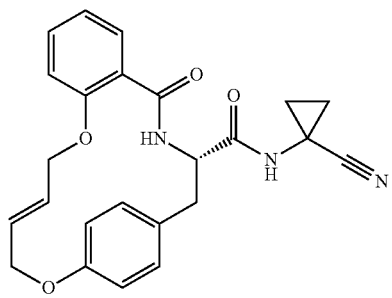 [SMILES: N#CC1(NC(=O)[C@@H]2Cc3ccc(cc3)OC/C=C/COc3ccccc3C(=O)N2)CC1]

In a 500 mL two-necked flask, Grubbs II catalyst (88.0 mg, 104 μmol, Eq: 0.3) was combined with dichloromethane (80 mL) to give a light brown solution. The solution was heated to 50° C. (reflux) under a nitrogen atmosphere. Now example 1C) (154 mg, 346 μmol, Eq: 1.00) dissolved in dry dichloromethane (40 mL) was dropwise transferred at reflux to the flask by a syringe. After complete addition, the color changes from light brown to dark brown. The solution was heated at reflux with stirring for 4 h. The reaction mixture was cooled to room temperature, filtered through silica filter, evaporated to dryness. The crude material was purified by preparative HPLC to yield a brown solid (29 mg; 20%). m/z=416.0 [M−H]$^-$.

Example 2

(E)-(S)-5-Oxo-11,16-dioxa-4-aza-tricyclo[15.2.2.1*6,10*]docosa-1(20),6,8,10(22),13,17(21),18-heptaene-3-carboxylic acid (1-cyano-cyclopropyl)-amide

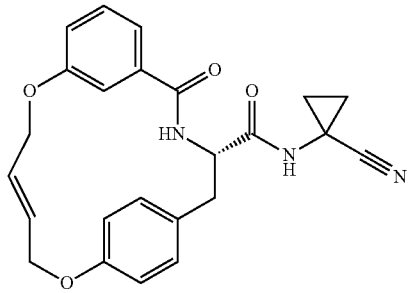 [SMILES: N#CC1(NC(=O)[C@@H]2Cc3ccc(cc3)OC/C=C/COc3cccc(c3)C(=O)N2)CC1]

The title compound was prepared in analogy to example 1 to yield a brown solid (6 mg; 7%). m/z=418.1759 [M+H]$^+$.

Example 3

(E)-(S)-5-Oxo-17-oxa-4-aza-tricyclo[16.2.2.0%6,11&]docosa-1(21),6,8,10,14,18(22),19-heptaene-3-carboxylic acid (1-cyano-cyclopropyl)-amide

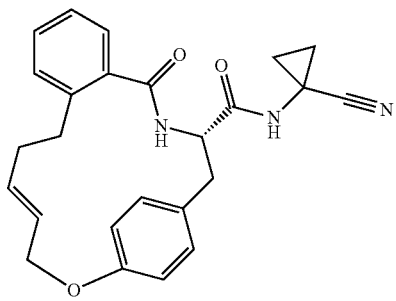 [SMILES: N#CC1(NC(=O)[C@@H]2Cc3ccc(cc3)OC/C=C/CCc3ccccc3C(=O)N2)CC1]

The title compound was prepared in analogy to example 1 with a reaction time of 24 h instead of 4 h in the last step to yield an off-white solid (3 mg; 2%). m/z=416.1973 [M+H]$^+$.

Example 4

(E)-(S)-19-Chloro-5-oxo-12,17-dioxa-4-aza-tricyclo[16.2.2.0*6,11*]docosa-1(21),6(11),7,9,14,18(22),19-heptaene-3-carboxylic acid (1-cyano-cyclopropyl)-amide

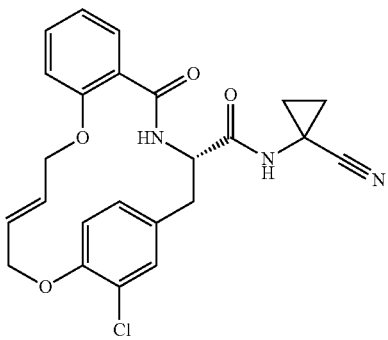 [SMILES: N#CC1(NC(=O)[C@@H]2Cc3ccc(c(Cl)c3)OC/C=C/COc3ccccc3C(=O)N2)CC1]

A) [(S)-2-(3-Chloro-4-hydroxy-phenyl)-1-(1-cyano-cyclopropylcarbamoyl)-ethyl]-carbamic acid tert-butyl ester

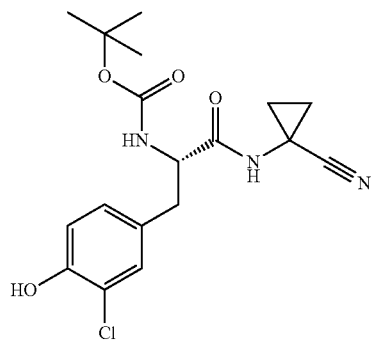 [SMILES: CC(C)(C)OC(=O)N[C@@H](Cc1ccc(O)c(Cl)c1)C(=O)NC1(C#N)CC1]

(S)-2-(tert-butoxycarbonylamino)-3-(3-chloro-4-hydroxyphenyl)propanoic acid (3.86 g, 12.2 mmol, Eq: 1.00) was dissolved in DMF (50 mL). HATU (9.3 g, 24.4 mmol, Eq: 2.00), 1-amino-1-cyclopropanecarbonitrile hydrochloride (1.74 g, 14.7 mmol, Eq: 1.20) and Hunig's Base (3.16 g, 4.27 mL, 24.4 mmol, Eq: 2.00) were added to the obtained suspension. The reaction mixture was stirred at 25° C. for 24 h. The reaction mixture was poured into aqueous 0.1M HCl (300 mL), extracted with dichloromethane (3×125 mL), dried over Na$_2$SO$_4$, filtered and evaporated. The crude material was purified by flash chromatography (silica gel, 80 g, 0% to 65% AcOEt in n-heptane) to yield a white solid (3.13 g; 67%). m/z=378.1 [M−H]$^-$.

B) [(S)-2-(4-Allyloxy-3-chloro-phenyl)-1-(1-cyano-cyclopropylcarbamoyl)-ethyl]-carbamic acid tert-butyl ester

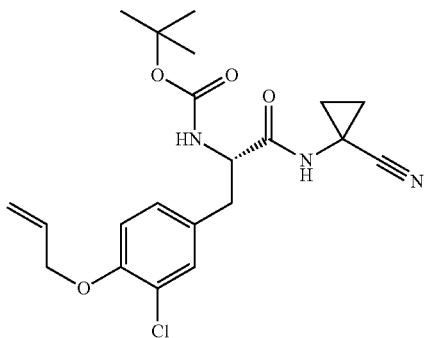 [SMILES: C=CCOc1ccc(C[C@H](NC(=O)OC(C)(C)C)C(=O)NC2(C#N)CC2)cc1Cl]

Example 4A) (3.13 g, 8.24 mmol, Eq: 1.00) was dissolved in dichloromethane (25 mL) and Hunig's base (2.66 g, 3.6 ml, 20.6 mmol, Eq: 2.50) and allyl bromide (1.2 g, 856 μL, 9.89 mmol, Eq: 1.2) were added. The reaction mixture was stirred 4 h at 25° C. After that, additional allyl bromide (598 mg, 428 μL, 4.94 mmol, Eq: 0.6) was added and the reaction mixture was stirred over night at 25° C. Again, allyl bromide (598 mg, 428 μL, 4.94 mmol, Eq: 0.6) was added and the reaction mixture was stirred over night at 40° C. After that, additional allyl bromide (598 mg, 428 μl, 4.94 mmol, Eq: 0.6) was added and the reaction mixture was stirred for 3 d at 40° C. The reaction mixture was cooled to room temperature and was extracted with aqueous 0.5N HCl—solution/CH$_2$Cl$_2$. The organic layers were dried over Na$_2$SO$_4$, filtered and concentrated in vacuo. The crude material was purified by flash chromatography (silica gel, 70 g, 0% to 60% AcOEt in heptane) to yield a white solid (1.9 g; 54%). m/z=420.2 [M+H]$^+$; 364.0 [M+H-tBu]$^+$; 320.0 [M+H-Boc]$^+$.

C) (E)-(S)-19-Chloro-5-oxo-12,17-dioxa-4-aza-tricyclo[16.2.2.0*6,11*]docosa-1(21),6(11),7,9,14,18(22),19-heptaene-3-carboxylic acid (1-cyano-cyclopropyl)-amide

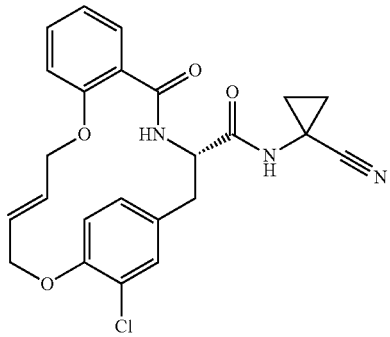 [SMILES: N#CC1(NC(=O)[C@@H]2Cc3ccc(c(Cl)c3)OC/C=C/COc3ccccc3C(=O)N2)CC1]

Starting from example 4B) the title compound was prepared in analogy to example 1 to yield an off-white solid (3 mg; 2%). m/z=416.1973 [M+H]$^+$.

Example 5

(E)-(S)-19-Chloro-5-oxo-17-oxa-4-aza-tricyclo[16.2.2.0*6,11*]docosa-1(21),6,8,10,14,18(22),19-heptaene-3-carboxylic acid (1-cyano-cyclopropyl)-amide

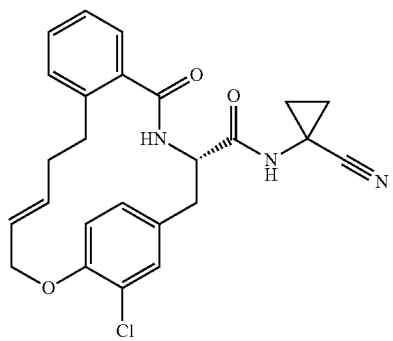 [SMILES: N#CC1(NC(=O)[C@@H]2Cc3ccc(c(Cl)c3)OC/C=C/CCc3ccccc3C(=O)N2)CC1]

Starting from example 4B) the title compound was prepared in analogy to example 1 to yield an off-white solid (5 mg; 3%). m/z=450.1 [M+H]$^+$.

Example 6

(E)-(S)-18-Chloro-5-oxo-11,16-dioxa-4-aza-tricyclo[15.2.2.1*6,10*]docosa-1(20),6,8,10(22),13,17(21),18-heptaene-3-carboxylic acid (1-cyano-cyclopropyl)-amide

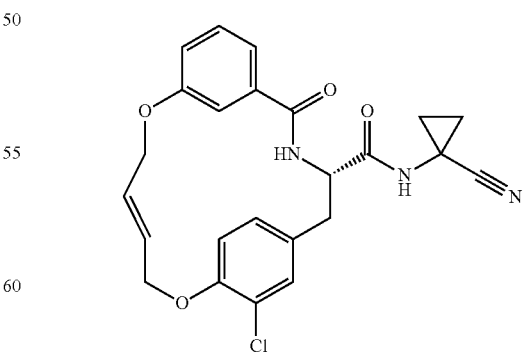

Starting from example 4B) the title compound was prepared in analogy to example 1 to yield a light yellow solid (75 mg; 35%). m/z=450.1 [M+H]$^+$.

Example 7

(S)-19-Chloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide

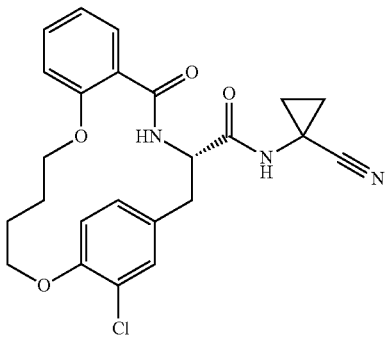 [SMILES: N#CC1(NC(=O)[C@@H]2Cc3ccc(c(Cl)c3)OCCCCOc3ccccc3C(=O)N2)CC1]

A) (S)-2-tert-Butoxycarbonylamino-3-(3-chloro-4-hydroxy-phenyl)-propionic acid methyl ester

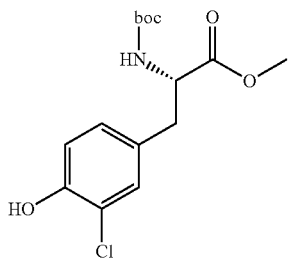

In a 10 mL round-bottomed flask, (S)-2-(tert-butoxycarbonylamino)-3-(3-chloro-4-hydroxyphenyl)propanoate dicyclohexylammonium salt (300 mg, 604 μmol, Eq: 1.00) was combined with dry THF (2 mL) to give a white suspension. LiOH hydrate (38.4 mg, 905 μmol, Eq: 1.50) was added and the mixture was stirred for 30 min at 25° C. Then Me$_2$SO$_4$ (80.1 mg, 60.7 μL, 604 μmol, Eq: 1.00) was added. The reaction mixture was heated to 80° C. and stirred for 2 h. After that the mixture was stirred for 18 h at 50° C. The crude reaction mixture was concentrated in vacuo. The reaction mixture was poured into saturated aqueous NaHCO$_3$ solution and extracted with AcOEt (2×). The organic layers were combined and washed with brine (1×). The organic layers were dried over Na$_2$SO$_4$ and concentrated in vacuo. The crude material was purified by flash chromatography (silica gel, 20 g, n-heptane/AcOEt 4/1, 3/1) to yield a colorless oil (132 mg; 66%). m/z=330.2 [M+H]$^+$; 274.1 [M+H-tBu]$^+$; 230.2 [M+H-Boc]$^+$.

B) (S)-3-(4-Allyloxy-3-chloro-phenyl)-2-tert-butoxycarbonylamino-propionic acid methyl ester

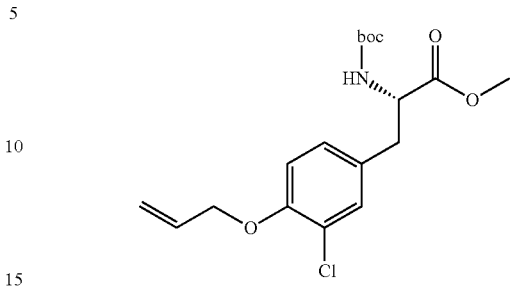

In a 10 mL round-bottomed flask, (S)-methyl 2-(tert-butoxycarbonylamino)-3-(3-chloro-4-hydroxyphenyl)propanoate (120 mg, 364 μmol, Eq: 1.00) was combined with DCM (4 mL) to give a colorless solution. Hunig's base (118 mg, 159 μL, 910 μmol, Eq: 2.50) and 3-bromoprop-1-ene (54.5 mg, 39.0 μL, 437 μmol, Eq: 1.20) were added. The reaction mixture was heated to 40° C. and stirred for 2 h. After that the mixture was heated for 20 h at 40° C. Additional allyl bromide (1.8 eq) was added and the mixture was stirred for additional 3 d at 40° C. The reaction mixture was poured into 0.1M aqueous HCl and extracted with DCM (2×). The organic layers were combined, washed with saturated aqueous NaHCO$_3$ (1×) solution and brine (1×). The organic layers were dried over Na$_2$SO$_4$ and concentrated in vacuo. The crude material was purified by flash chromatography (silica gel, 20 g, n-heptane/AcOEt 4/1) to yield a colorless oil (100 mg, 74%). m/z=370.2 [M+H]$^+$; 270.3 [M+H-Boc]$^+$.

C) (S)-3-(4-Allyloxy-3-chloro-phenyl)-2-amino-propionic acid methyl ester

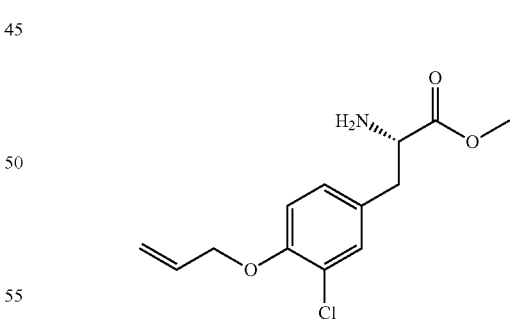

In a 10 mL round-bottomed flask, (S)-methyl 3-(4-(allyloxy)-3-chlorophenyl)-2-(tert-butoxycarbonylamino)propanoate (90 mg, 243 μmol, Eq: 1.00) was combined with formic acid (1.12 g, 933 μL, 24.3 mmol, Eq: 100) and stirred at RT for 3 h. The crude reaction mixture was concentrated in vacuo. The reaction mixture was neutralised with 5% aqueous Na$_2$CO$_3$ and extracted with DCM (3×). The organic layers were combined and dried over Na$_2$SO$_4$ and concentrated in vacuo to yield a colorless oil (68 mg; 100%). m/z=270.3 [M+H]$^+$; 292.1 [M+Na]$^+$.

D) (S)-2-(2-Allyloxy-benzoylamino)-3-(4-allyloxy-3-chloro-phenyl)-propionic acid methyl ester

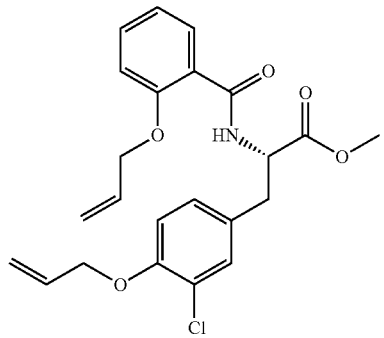 [SMILES: C=CCOc1ccc(C[C@H](NC(=O)c2ccccc2OCC=C)C(=O)OC)cc1Cl]

In a 10 mL round-bottomed flask, (S)-methyl 3-(4-(allyloxy)-3-chlorophenyl)-2-aminopropanoate (65 mg, 241 µmol, Eq: 1.00) was combined with DMF (2 mL) to give a colorless solution. 2-(allyloxy)benzoic acid (54.2 mg, 289 µmol, Eq: 1.20), HATU (183 mg, 482 µmol, Eq: 2.00) and Hunig's base (62.3 mg, 84.2 µL, 482 µmol, Eq: 2.00) were added. The reaction mixture was stirred at 22° C. for 16 h. The reaction mixture was poured into saturated aqueous NaHCO$_3$ solution and extracted with DCM (2×). The organic layers were combined, washed with 0.1M aqueous HCl (1×), water (3×), and brine (1×). The organic layers were dried over Na$_2$SO$_4$ and concentrated in vacuo. The crude material was purified by flash chromatography (silica gel, 10 g, n-heptane/AcOEt 4/1) to yield a light yellow oil (96 mg; 93%). m/z=430.2 [M+H]$^+$.

E) (E)-(S)-19-Chloro-5-oxo-12,17-dioxa-4-aza-tricyclo[16.2.2.0*6,11*]docosa-1(21),6,8,10,14,18(22),19-heptaene-3-carboxylic acid methyl ester

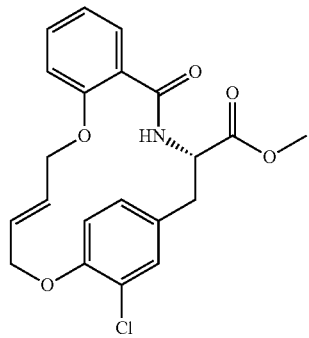 [SMILES: COC(=O)[C@@H]1Cc2ccc(c(Cl)c2)OC/C=C/COc2ccccc2C(=O)N1]

In a 250 mL three-necked flask, Grubbs II catalyst (56.3 mg, 66.3 µmol, Eq: 0.30) was combined with dry DCM (50 mL) to give a brown solution. The reaction mixture was heated to 50° C. (reflux) under argon atmosphere. (S)-methyl 3-(4-(allyloxy)-3-chlorophenyl)-2-(2-(allyloxy)benzamido)propanoate (95 mg, 221 µmol, Eq: 1.00) dissolved in dry DCM (30 mL) was added dropwise. The reaction mixture was stirred at 50° C. for 2 h under argon atmosphere. The reaction mixture was stirred for 1 h at 50° C. to drive the reaction to completion. The crude reaction mixture was concentrated in vacuo and purified by flash chromatography (silica gel, 10 g, n-heptane/AcOEt 4/1, 3/1) to yield a brown oil (42 mg; 47%). m/z=402.2 [M+H]$^+$.

F) (S)-19-Chloro-5-oxo-12,17-dioxa-4-aza-tricyclo[16.2.2.0*6,11*]docosa-1(21),6,8,10,18 (22),19-hexaene-3-carboxylic acid methyl ester

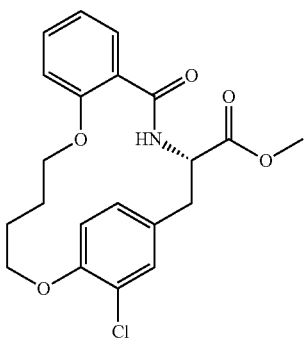 [SMILES: COC(=O)[C@@H]1Cc2ccc(c(Cl)c2)OCCCCOc2ccccc2C(=O)N1]

In a 10 mL round-bottomed flask, example 7E) (42 mg, 105 µmol, Eq: 1.00) was combined with AcOEt (2 mL) to give a brown solution. Pd/C 10% (11.1 mg, 10.5 µmol, Eq: 0.10) was added. The reaction mixture was stirred vigorously at 22° C. for 2 h under a H$_2$ atmosphere. The reaction mixture was filtered through a paper. It was washed several times with AcOEt and the solvent was evaporated to dryness to yield a black oil (38 mg; 90%). m/z=404.3 [M+H]$^+$.

G) (S)-19-Chloro-5-oxo-12,17-dioxa-4-aza-tricyclo[16.2.2.0*6,11*]docosa-1(21),6,8,10,18(22),19-hexaene-3-carboxylic acid

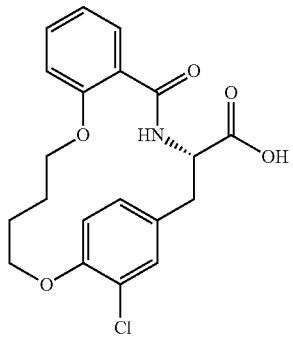 [SMILES: O=C1N[C@H](C(=O)O)Cc2ccc(c(Cl)c2)OCCCCOc2ccccc21]

In a 10 mL round-bottomed flask, example 7F) (38 mg, 94.1 µmol, Eq: 1.00) was combined with THF (1.5 mL) and water (1 mL) to give a grey solution. Lithium hydroxide hydrate (4.79 mg, 113 µmol, Eq: 1.20) was added. The reaction mixture was stirred at 22° C. for 3 h under an argon atmosphere. The crude reaction mixture was concentrated in vacuo. The reaction mixture was poured into 1M aqueous HCl until pH=1-2 was reached and then extracted with DCM (4×). The organic layers were dried over Na$_2$SO$_4$ and concentrated in vacuo to yield a brown gum (35 mg; 95%). m/z=388.1 [M−H]$^-$.

H) (S)-19-Chloro-5-oxo-12,17-dioxa-4-aza-tricyclo[16.2.2.0*6,11*]docosa-1 (24),6,8,10,18(22),19-hexaene-3-carboxylic acid (1-cyano-cyclopropyl)-amide

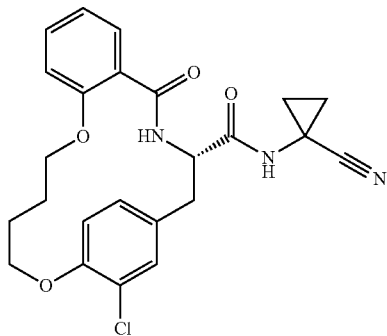 [SMILES: N#CC1(NC(=O)[C@@H]2Cc3ccc(c(Cl)c3)OCCCCOc3ccccc3C(=O)N2)CC1]

In a 10 mL round-bottomed flask, example 7G) (35 mg, 89.8 μmol, Eq: 1.00) was combined with DMF (1 mL) to give a light brown solution. HATU (68.3 mg, 180 μmol, Eq: 2.00), 1-aminocyclopropanecarbonitrile hydrochloride (13.0 mg, 108 μmol, Eq: 1.20) and Hunig's base (40.6 mg, 54.9 μL, 314 μmol, Eq: 3.50) were added. The reaction mixture was stirred at 22° C. for 20 h. The reaction mixture was poured into saturated aqueous NaHCO$_3$ solution and extracted with DCM (2×). The organic layers were combined, washed with water (3×) and brine (1×). The organic layers were dried over Na$_2$SO$_4$ and concentrated in vacuo. The crude material was purified by flash chromatography (silica gel, 10 g, n-heptane/AcOEt 1/1) and preparative HPLC to yield a light brown powder (11 mg; 27%). m/z=454.2 [M+H]$^+$.

Example 8

(E)-(S)-8-Bromo-19-chloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide

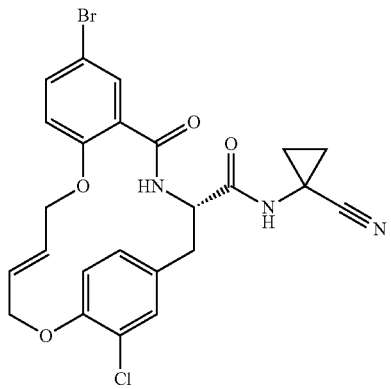 [SMILES: N#CC1(NC(=O)[C@@H]2Cc3ccc(c(Cl)c3)OC/C=C/COc3ccc(Br)cc3C(=O)N2)CC1]

A) (S)-2-(2-Allyloxy-5-bromo-benzoylamino)-3-(4-allyloxy-3-chloro-phenyl)-propionic acid methyl ester

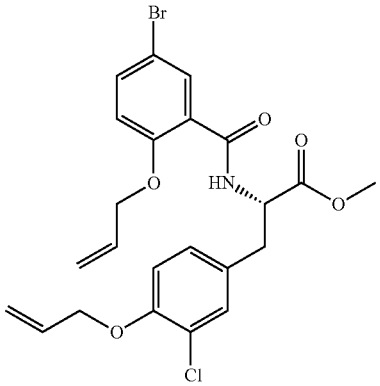 [SMILES: C=CCOc1ccc(C[C@H](NC(=O)c2cc(Br)ccc2OCC=C)C(=O)OC)cc1Cl]

The compound was prepared in analogy to example 7D) to yield a yellow oil (72%). m/z=510.0502 [M+H]$^+$.

B) (S)-2-(2-Allyloxy-5-bromo-benzoylamino)-3-(4-allyloxy-3-chloro-phenyl)-propionic acid

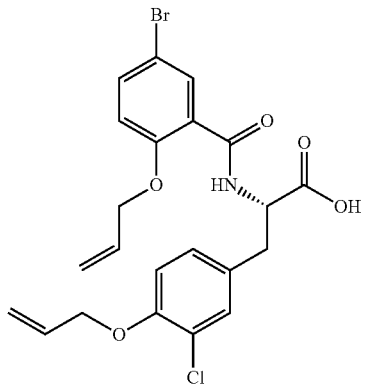 [SMILES: C=CCOc1ccc(C[C@H](NC(=O)c2cc(Br)ccc2OCC=C)C(=O)O)cc1Cl]

In a 10 mL round-bottomed flask, example 8A) (140 mg, 275 μmol, Eq: 1.00) was combined with THF (1.5 mL) and water (1.5 mL) to give a colorless solution. Lithium hydroxide hydrate (14.0 mg, 330 μmol, Eq: 1.20) was added. The reaction mixture was stirred at 22° C. for 24 h under Ar atmosphere. The crude reaction mixture was concentrated in vacuo. After that, the mixture neutralised with aqueous HCl (1N) until pH=1-2 was reached. After that the mixture was extracted four times with DCM. The organic layers were dried over Na$_2$SO$_4$ and concentrated in vacuo to yield a yellow oil (148 mg; 100%). m/z=496.0 [M+H]$^+$.

C) 2-Allyloxy-N—[(S)-2-(4-allyloxy-3-chloro-phenyl)-1-(1-cyano-cyclopropylcarbamoyl)-ethyl]-5-bromo-benzamide

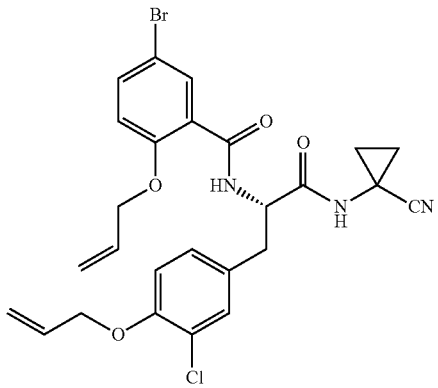 [SMILES: C=CCOc1ccc(C[C@H](NC(=O)c2cc(Br)ccc2OCC=C)C(=O)NC2(C#N)CC2)cc1Cl]

In a 10 mL round-bottomed flask, example 8B) (140 mg, 283 µmol, Eq: 1.00) was combined with DMF (2 ml) to give a light yellow solution. HATU (215 mg, 566 µmol, Eq: 2.00), 1-aminocyclopropanecarbonitrile hydrochloride (40.3 mg, 340 µmol, Eq: 1.20) and Hunig's base (128 mg, 173 µL, 990 µmol, Eq: 3.50) were added. The reaction mixture was stirred at 22° C. for 16 h. The reaction mixture was poured into an aqueous saturated NaHCO$_3$ solution and extracted with DCM (two times). The organic layers were combined, washed with water (3×) and brine (1×). The organic layers were dried over Na$_2$SO$_4$ and concentrated in vacuo. The crude material was purified by flash chromatography (silica gel, 20 g, n-heptane/AcOEt 9/1, 4/1, 2/1) to yield a yellow solid (40 mg; 25%). m/z=560.0758 [M+H]$^+$.

D) (E)-(S)-8-Bromo-19-chloro-5-oxo-12,17-dioxa-4-aza-tricyclo[16.2.2.0*6,11*]docosa-1(24),6,8,10,14,18(22),19-heptaene-3-carboxylic acid (1-cyano-cyclopropyl)-amide

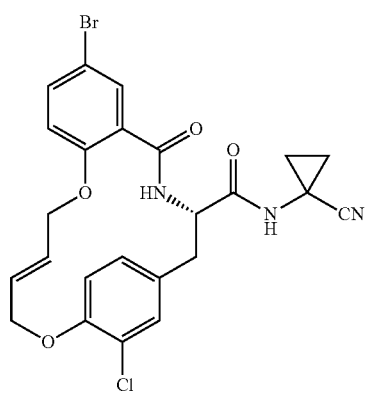 [SMILES: N#CC1(NC(=O)[C@@H]2Cc3ccc(c(Cl)c3)OC/C=C/COc3ccc(Br)cc3C(=O)N2)CC1]

In a 100 mL three-necked flask, Grubbs II (16.4 mg, 19.3 µmol, Eq: 0.30) was combined with dry DCM (15 mL) to give a brown solution. The reaction mixture was heated to 50° C. and example 8C) (36 mg, 64.4 µmol, Eq: 1.00) dissolved in DCM (15 mL), was added dropwise very slowly (25 min). The reaction mixture was heated to 50° C. and stirred for 2 h. The crude reaction mixture was concentrated in vacuo. The crude material was purified by flash chromatography (silica gel, 10 g, n-heptane/AcOEt 2/1, 1/1) to yield a brown solid (18 mg, 53%). m/z=532.0 [M+H]$^+$.

Example 9

(S)-8-Bromo-19-chloro-5-oxo-12,17-dioxa-4-aza-tricyclo[16.2.2.0%6,11&]docosa-1(21),6,8,10,18(22),19-hexaene-3-carboxylic acid (1-cyano-cyclopropyl)-amide

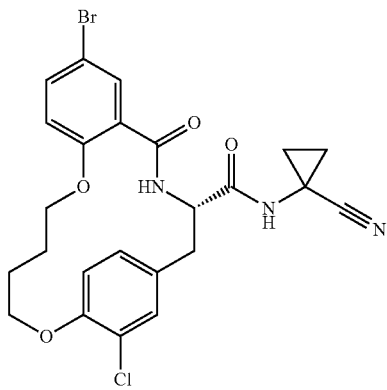 [SMILES: N#CC1(NC(=O)[C@@H]2Cc3ccc(c(Cl)c3)OCCCCOc3ccc(Br)cc3C(=O)N2)CC1]

In a 10 mL round-bottomed flask, example 8D) (15 mg, 28.3 µmol, Eq: 1.00) was combined with ethyl acetate (1 mL) to give a light brown solution. Pd/C 10% (3.01 mg, 2.83 µmol, Eq: 0.10) was added. The reaction mixture was stirred at 22° C. for 4 h under H$_2$ atmosphere. The reaction mixture was filtered through paper and washed several times with AcOEt. The filtrate was concentrated in vacuo. The crude material was purified by flash chromatography (silica gel, 5 g, n-heptane/AcOEt 2/1, 1/1, 1/2) to yield a light brown solid (8 mg; 53%). m/z=534.0 [M+H]$^+$.

Example 10

(E)-(S)-8,19-Dichloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide

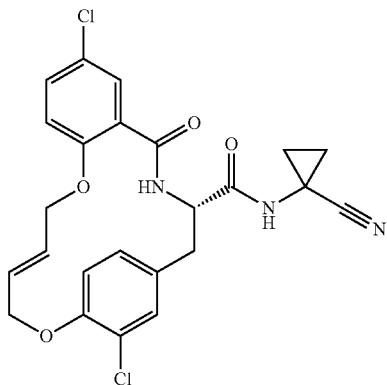 [SMILES: N#CC1(NC(=O)[C@@H]2Cc3ccc(c(Cl)c3)OC/C=C/COc3ccc(Cl)cc3C(=O)N2)CC1]

The title compound was prepared in analogy to example 8 to yield a brown solid (22 mg; 45%). m/z=486.2 [M+H]$^+$.

Example 11

(S)-8,19-Dichloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide

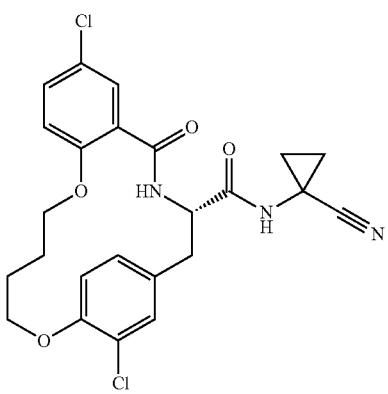 [SMILES: N#CC1(NC(=O)[C@@H]2Cc3ccc(c(Cl)c3)OCCCCOc3ccc(Cl)cc3C(=O)N2)CC1]

The title compound was prepared in analogy to example 9 to yield a brown solid (9 mg; 56%). m/z=488.2 [M+H]⁺.

Example 12

(E)-(S)-18-Chloro-5-oxo-16-oxa-4,10-diaza-tricyclo[15.2.2.0*6,10*]henicosa-1(20),13,17(21),18-tetraene-3-carboxylic acid (1-cyano-cyclopropyl)-amide

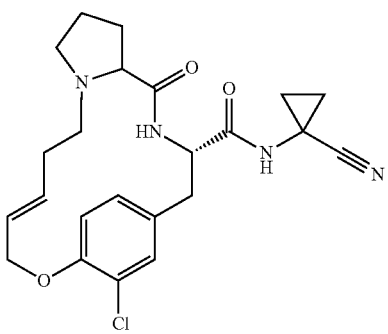 [SMILES: N#CC1(NC(=O)[C@@H]2Cc3ccc(c(Cl)c3)OC/C=C/CCN3CCCC3C(=O)N2)CC1]

A) (S)-2-[(S)-2-(4-Allyloxy-3-chloro-phenyl)-1-methoxycarbonyl-ethylcarbamoyl]-pyrrolidine-1-carboxylic acid tert-butyl ester

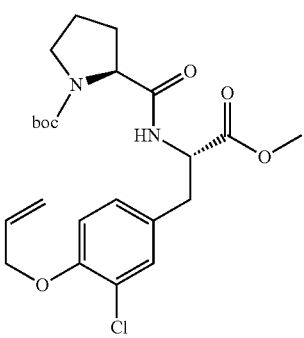

In a 25 mL round-bottomed flask, (S)-1-(tert-butoxycarbonyl)pyrrolidine-2-carboxylic acid (279 mg, 1.3 mmol, Eq: 1.00) and (S)-methyl 3-(4-(allyloxy)-3-chlorophenyl)-2-aminopropanoate (350 mg, 1.3 mmol, Eq: 1.00) were combined with DMF (6 mL) to give a colorless solution. HATU (986 mg, 2.59 mmol, Eq: 2.00) and Hunig's base (335 mg, 453 μL, 2.59 mmol, Eq: 2.00) were added. The reaction mixture was stirred at 25° C. for 20 h. The reaction mixture was poured into saturated aqueous NaHCO₃ solution and extracted with DCM (2×). The organic layers were combined, washed with water (3×) and brine (1×). The organic layers were dried over Na₂SO₄ and concentrated in vacuo. The crude material was purified by flash chromatography (silica gel, 20 g, n-heptane/AcOEt 3/1, 2/1) to yield a yellow oil (570 mg; 94%). m/z=467.2 [M+H]⁺; 367.1 [M+H-Boc]⁺.

B) (S)-3-(4-Allyloxy-3-chloro-phenyl)-2-[((S)-pyrrolidine-2-carbonyl)-amino]-propionic acid methyl ester

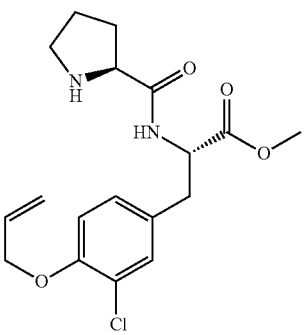 [SMILES: C=CCOc1ccc(C[C@H](NC(=O)[C@@H]2CCCN2)C(=O)OC)cc1Cl]

In a 10 mL round-bottomed flask, example 12A) (570 mg, 1.22 mmol, Eq: 1.00) was combined with formic acid (5.62 g, 4.68 mL, 122 mmol, Eq: 100). The reaction mixture was stirred at 25° C. for 24 h. The crude reaction mixture was concentrated in vacuo. The reaction mixture was basified with 5% aqueous Na₂CO₃ solution and extracted with DCM (4×). The organic layers were dried over Na₂SO₄ and concentrated in vacuo to yield a yellow oil (328 mg; 73%). m/z=367.1 [M+H]⁺.

C) (S)-3-(4-Allyloxy-3-chloro-phenyl)-2-[((S)-1-but-3-enyl-pyrrolidine-2-carbonyl)-amino]-propionic acid methyl ester

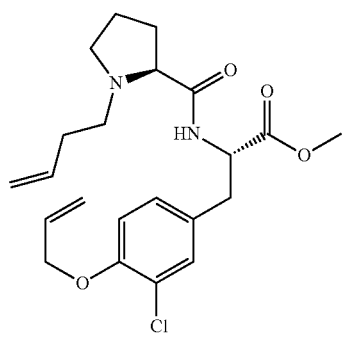 [SMILES: C=CCCN1CCC[C@H]1C(=O)N[C@@H](Cc1ccc(OCC=C)c(Cl)c1)C(=O)OC]

In a 10 mL round-bottomed flask, example 12B) (312 mg, 851 μmol, Eq: 1.00) was combined with acetonitrile (6.00 mL) to give a light brown solution. Hunig's base (132 mg, 178 μL, 1.02 mmol, Eq: 1.20) and 4-bromobut-1-ene (141 mg, 106 μL, 1.02 mmol, Eq: 1.20) was added. The reaction mixture was stirred at 75° C. for 24 h. The crude reaction mixture was concentrated in vacuo. The reaction mixture was poured into a 5% aqueous Na$_2$CO$_3$ solution and extracted with DCM (2×). The organic layers were combined, washed with water (1×) and brine (1×). The organic layers were dried over Na$_2$SO$_4$ and concentrated in vacuo. The crude material was purified by flash chromatography (silica gel, 20 g, n-heptane/AcOEt 3/1, 2/1, 1/1) to yield a yellow oil (210 mg; 59%). m/z=421.1 [M+H]$^+$.

D) (E)-(S)-18-Chloro-5-oxo-16-oxa-4,10-diaza-tricyclo[15.2.2.0*6,10*]henicosa-1(20),13,17(21),18-tetraene-3-carboxylic acid methyl ester

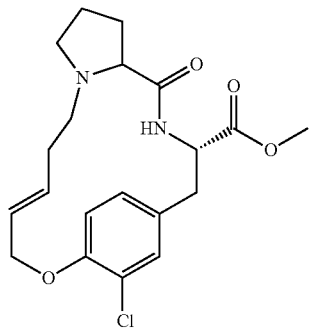 [SMILES: COC(=O)[C@@H]1Cc2ccc(c(Cl)c2)OC/C=C/CCN2CCCC2C(=O)N1]

Example 12C) (100 mg, 238 μmol, Eq: 1.00)) was diluted in dry degassed DCM (10 mL) under a nitrogen atmosphere and para-toluenesulfonic acid (12% in acetic acid) (682 mg, 637 μL, 475 μmol, Eq: 2.00) was added. The reaction mixture was stirred at 45° C. for 30 min. After that, the colorless solution was added dropwise via syringe (15 min) to a brown solution of Grubbs II catalyst (60.5 mg, 71.3 μmol, Eq: 0.30) dissolved in dry degassed DCM (80 mL) at reflux under a nitrogen atmosphere. The reaction mixture was stirred at 50° C. for 2 h. The reaction mixture was poured into an aqueous 5% Na$_2$CO$_3$ solution and extracted with DCM (3×). The organic layers were dried over Na$_2$SO$_4$ and concentrated in vacuo. The crude material was purified by flash chromatography (silica gel, 20 g, DCM, DCM/MeOH 99/1, 98/2) to yield a brown gum (81 mg; 87%) as mixture of epimers. m/z=393.1575 [M+H]$^+$ (mixture of epimers).

E) (E)-(S)-18-Chloro-5-oxo-16-oxa-4,10-diaza-tricyclo[15.2.2.0*6,10*]henicosa-1(20),13,17(21),18-tetraene-3-carboxylic acid with lithium chloride

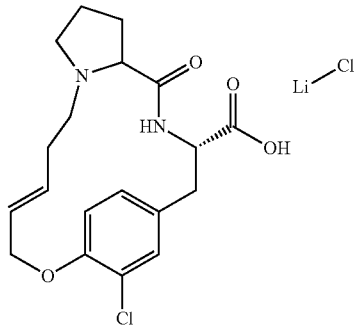

In a 10 mL round-bottomed flask, example 12D) (80 mg, 204 μmol, Eq: 1.00) was combined with THF (2 mL) and water (2 mL) to give a brown solution. Lithium hydroxide hydrate (12.9 mg, 305 mmol, Eq: 1.50) was added to the solution. The reaction mixture was stirred at 25° C. for 4 h. The crude reaction mixture was concentrated in vacuo. The water phase remaining was neutralised to pH=1-2 with aqueous 1N HCl. The mixture was evaporated to dryness to yield a brown solid (91 mg; 100%). m/z=379.2 [M+H]$^+$.

F) (E)-(S)-18-Chloro-5-oxo-16-oxa-4,10-diaza-tricyclo[15.2.2.0*6,10*]henicosa-1(20),13,17(21),18-tetraene-3-carboxylic acid (1-cyano-cyclopropyl)-amide

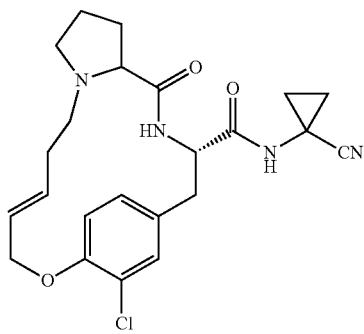 [SMILES: N#CC1(NC(=O)[C@@H]2Cc3ccc(c(Cl)c3)OC/C=C/CCN3CCCC3C(=O)N2)CC1]

In a 10 mL round-bottomed flask, example 12E (90 mg) was combined with DMF (3 mL) to give a brown solution. HATU (162 mg, 427 μmol, Eq: 2.00), 1-aminocyclopropanecarbonitrile hydrochloride (31.0 mg, 256 μmol, Eq: 1.20) and Hunig's base (138 mg, 187 μL, 1.07 mmol, Eq: 5.00) were added. The reaction mixture was stirred at 25° C. for 16 h. The reaction mixture was poured into saturated aqueous NaHCO$_3$ solution and extracted with DCM (2×). The organic layers were combined, washed with water (3×) and brine (1×). The organic layers were dried over Na$_2$SO$_4$ and concentrated in vacuo. The crude material was purified by flash chromatography (silica gel, 10 g, DCM/MeOH 99/1, 98/2) and preparative HPLC to yield a yellow solid (7 mg; 8%). m/z=443.4 [M+H]$^+$.

Example 13

(E)-(3S,8S)-18-Chloro-8-fluoro-5-oxo-16-oxa-4,10-diaza-tricyclo[15.2.2.0*6,10*]henicosa-1(20),13,17(21),18-tetraene-3-carboxylic acid (1-cyano-cyclopropyl)-amide

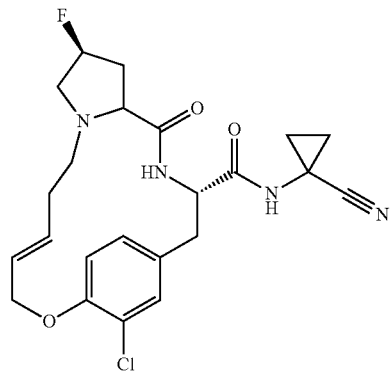 [SMILES: N#CC1(NC(=O)[C@@H]2Cc3ccc(c(Cl)c3)OC/C=C/CCN3C[C@@H](F)CC3C(=O)N2)CC1]

A) (2S,4S)-1-But-3-enyl-4-fluoro-pyrrolidine-2-carboxylic acid methyl ester

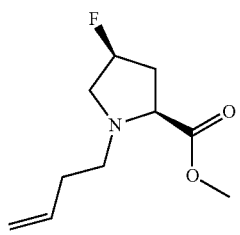

In a 25 mL round-bottomed flask, (2S,4S)-methyl 4-fluoro-pyrrolidine-2-carboxylate hydrochloride (160 mg, 871 µmol, Eq: 1.00) was combined with acetonitrile (3 mL) to give a white suspension. Hunig's base (282 mg, 380 µL, 2.18 mmol, Eq: 2.50) and 4-bromobut-1-ene (144 mg, 108 µL, 1.05 mmol, Eq: 1.20) were added sequentially. The reaction mixture was stirred at 70° C. for 2 days. The crude reaction mixture was concentrated in vacuo. The reaction mixture was poured into an aqueous 5% Na$_2$CO$_3$ solution and extracted with DCM (2×). The organic layers were combined, washed with brine (1×), the organic layers were dried over Na$_2$SO$_4$ and concentrated in vacuo to yield a yellow liquid (160 mg; 91%). m/z=202.2 [M+H]$^+$.

B) (2S,4S)-1-But-3-enyl-4-fluoro-pyrrolidine-2-carboxylic acid; compound with lithium chloride

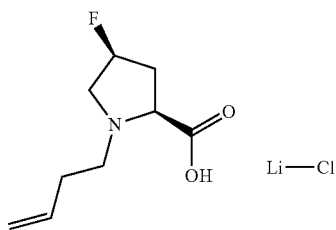

In a 10 mL round-bottomed flask, example 13A) (150 mg, 745 µmol, Eq: 1.00) was combined with THF (1.5 mL) and water (1.5 mL). Lithium hydroxide hydrate (37.9 mg, 894 µmol, Eq: 1.20) was added. The reaction mixture was stirred at 25° C. for 16 h. The crude reaction mixture was concentrated in vacuo and acidified with aqueous 1N HCl until pH=1.5 was reached. The crude product was evaporated to dryness to yield a light brown oil (237 mg; 97%). m/z=188.2 [M+H]$^+$.

C) (S)-3-(4-Allyloxy-3-chloro-phenyl)-2-tert-butoxycarbonylamino-propionic acid

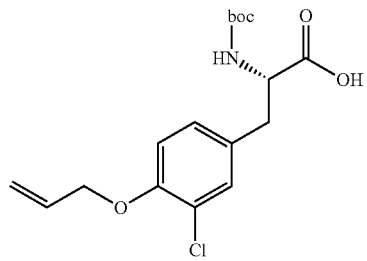

In a 25 mL round-bottomed flask, example 7B) (308 mg, 833 µmol, Eq: 1.00) was combined with THF (3 mL) and water (5.00 mL) to give a colorless solution. Lithium hydroxide hydrate (42.4 mg, 0.999 mmol, Eq: 1.20) was added. The reaction mixture was stirred for 2 h at 25° C. The crude reaction mixture was concentrated in vacuo. Then the reaction mixture was acidified to pH=1 with aqueous 1N HCl solution. The mixture was extracted with DCM (4×). The organic layers were dried over Na$_2$SO$_4$ and concentrated in vacuo to yield a white gum (286 mg; 97%). m/z=354.3 [M+H]$^+$.

D) [(S)-2-(4-Allyloxy-3-chloro-phenyl)-1-(1-cyano-cyclopropylcarbamoyl)-ethyl]-carbamic acid tert-butyl ester

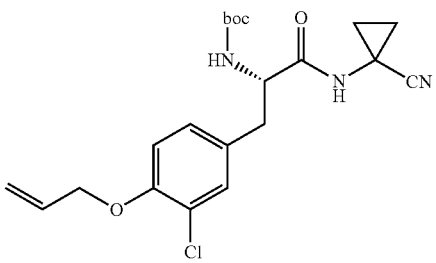

In a 25 mL round-bottomed flask, example 13C) (285 mg, 801 µmol, Eq: 1.00) was combined with DMF (6 mL) to give a colorless solution. HATU (609 mg, 1.6 mmol, Eq: 2.00), 1-aminocyclopropanecarbonitrile hydrochloride (115 mg, 961 µmol, Eq: 1.20) and Hunig's base (362 mg, 490 µL, 2.8 mmol, Eq: 3.50) were added. The reaction mixture was stirred at 25° C. for 16 h. The reaction mixture was poured into aqueous saturated NaHCO$_3$ solution and extracted with DCM (2×). The organic layers were combined, washed with water (3×) and brine (1×). The organic layers were dried over Na$_2$SO$_4$ and concentrated in vacuo. The crude material was purified by flash chromatography (silica gel, 20 g, n-heptane/AcOEt 3/1, 2/1) to yield an off-white solid (318 mg; 95%). m/z=420.2 [M+H]$^+$.

E) (S)-3-(4-Allyloxy-3-chloro-phenyl)-2-amino-N-(1-cyano-cyclopropyl)-propionamide

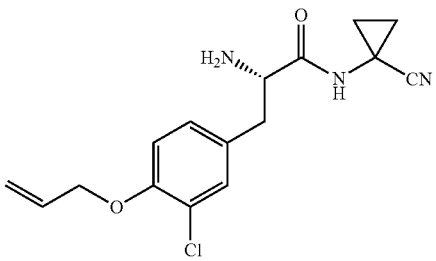 [SMILES: C=CCOc1ccc(C[C@H](N)C(=O)NC2(C#N)CC2)cc1Cl]

In a 10 mL round-bottomed flask, example 13D) (300 mg, 714 µmol, Eq: 1.00) was combined with formic acid (3.29 g, 2.74 mL, 71.4 mmol, Eq: 100). The reaction mixture was stirred at 25° C. for 16 h. The crude reaction mixture was concentrated in vacuo. The reaction mixture was poured into an aqueous 5% Na$_2$CO$_3$ solution and extracted with DCM (4×). The organic layers were dried over Na$_2$SO$_4$ and concentrated in vacuo to yield a yellow gum (220 mg; 96%). m/z=320.1 [M+H]$^+$.

F) (S)-1-But-3-enyl-4-fluoro-pyrrolidine-2-carboxylic acid [(S)-2-(4-allyloxy-3-chloro-phenyl)-1-(1-cyano-cyclopropylcarbamoyl)-ethyl]-amide

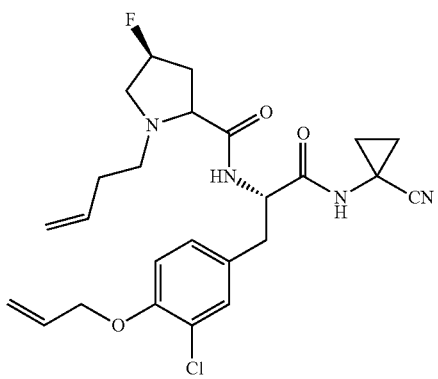 [SMILES: C=CCCN1C[C@@H](F)CC1C(=O)N[C@@H](Cc1ccc(OCC=C)c(Cl)c1)C(=O)NC1(C#N)CC1]

In a 10 mL round-bottomed flask, example 13B) (164 mg, 497 µmol, Eq: 1.50) was combined with DMF (3 mL). HATU (252 mg, 663 µmol, Eq: 2.00), example 13E) (106 mg, 331 µmol, Eq: 1.00) and Hunig's base (150 mg, 203 µL, 1.16 mmol, Eq: 3.50) were added. The reaction mixture was stirred at 25° C. for 16 h. The reaction mixture was poured into an aqueous saturated NaHCO$_3$ solution and extracted with DCM (2×). The organic layers were combined, washed with water (3×) and sat NaCl (1×). The organic layers were dried over Na$_2$SO$_4$ and concentrated in vacuo. The crude material was purified by flash chromatography (silica gel, 20 g, DCM/MeOH 98/2) to yield a yellow oil (119 mg; 73%) as a mixture of epimers. m/z=489.2 [M+H]$^+$.

G) (E)-(3S,8S)-18-Chloro-8-fluoro-5-oxo-16-oxa-4,10-diaza-tricyclo[15.2.2.0*6,10*]henicosa-1(20),13,17(21),18-tetraene-3-carboxylic acid (1-cyano-cyclopropyl)-amide

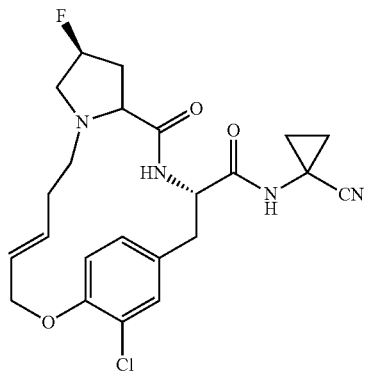 [SMILES: N#CC1(NC(=O)[C@@H]2Cc3ccc(c(Cl)c3)OC/C=C/CCN3C[C@@H](F)CC3C(=O)N2)CC1]

The title compound was prepared in analogy to example 12D) to yield a yellow gum (3.5 mg; 4%) as a mixture of epimers. m/z=461.3 [M+H]$^+$.

Example 14

(E)-(S)-18-Chloro-8,8-difluoro-5-oxo-16-oxa-4,10-diaza-tricyclo[15.2.2.0*6,10*]henicosa-1(20),13,17(21),18-tetraene-3-carboxylic acid (1-cyano-cyclopropyl)-amide

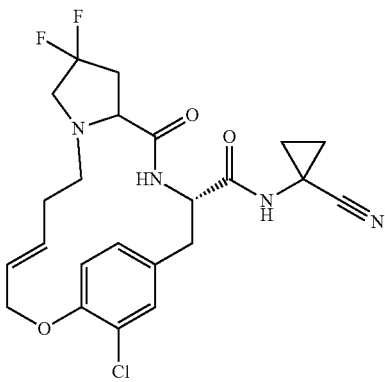 [SMILES: N#CC1(NC(=O)[C@@H]2Cc3ccc(c(Cl)c3)OC/C=C/CCN3CC(F)(F)CC3C(=O)N2)CC1]

The title compound was prepared in analogy to example 13 to yield a yellow oil (7 mg; 13%) as a mixture of epimers. m/z=479.1647 [M+H]$^+$.

Example 15

(E)-(S)-18-Chloro-8,8-dimethyl-5-oxo-16-oxa-4,10-diaza-tricyclo[15.2.2.0*6,10*]henicosa-1(20),13,17(21),18-tetraene-3-carboxylic acid (1-cyano-cyclopropyl)-amide

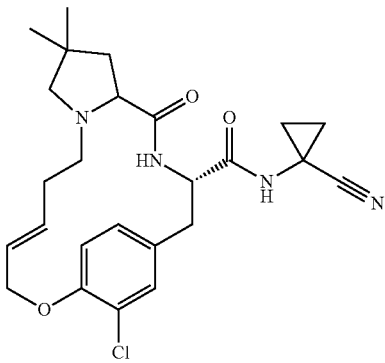 [SMILES: CC1(C)CC2C(=O)N[C@H](C(=O)NC3(C#N)CC3)Cc3ccc(c(Cl)c3)OC/C=C/CCN2C1]

The title compound was prepared in analogy to example 13 to yield a yellow oil (7 mg; 13%) as a mixture of epimers. m/z=471.2156 [M+H]$^+$.

Example 16

(E)-(S)-19-Chloro-8-methoxy-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide

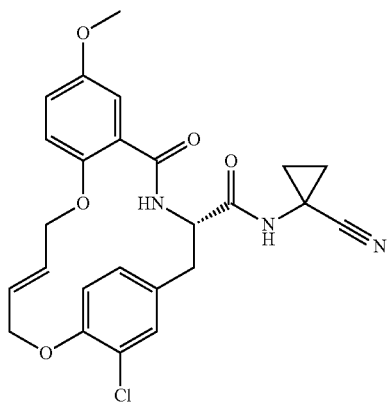 [SMILES: COc1ccc2c(c1)C(=O)N[C@H](C(=O)NC1(C#N)CC1)Cc1ccc(c(Cl)c1)OC/C=C/CO2]

The title compound was prepared in analogy to example 8 to yield a brown solid (49 mg; 52%). m/z=482.3 [M+H]$^+$.

Example 17

(S)-19-Chloro-8-methoxy-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide

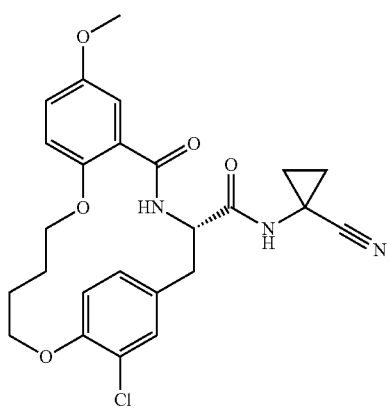 [SMILES: COc1ccc2c(c1)C(=O)N[C@H](C(=O)NC1(C#N)CC1)Cc1ccc(c(Cl)c1)OCCCCO2]

The title compound was prepared in analogy to example 9 to yield an off-white solid (23 mg; 64%). m/z=484.4 [M+H]$^+$.

Example 18

(E)-(S)-19-Chloro-9-methoxy-5-oxo-17-oxa-4-aza-tricyclo[16.2.2.0*6,11*]docosa-1(21),6,8,10,14,18(22),19-heptaene-3-carboxylic acid (1-cyano-cyclopropyl)-amide

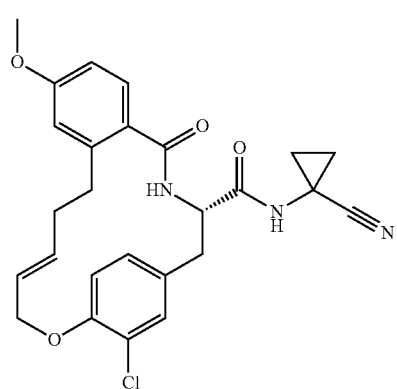 [SMILES: COc1ccc2c(c1)CC/C=C/COc1ccc(cc1Cl)C[C@@H](C(=O)NC1(C#N)CC1)NC2=O]

The title compound was prepared in analogy to example 8 starting from 2-(but-3-enyl)-4-methoxybenzoic acid to yield a brown solid (43 mg; 48%). m/z=480.2 [M+H]$^+$.

Example 19

(E)-(S)-19-Chloro-9-methyl-5-oxo-17-oxa-12-thia-4,10-diaza-tricyclo[16.2.2.0*6,11*]docosa-1(21),6,8,10,14,18(22),19-heptaene-3-carboxylic acid (1-cyano-cyclopropyl)-amide

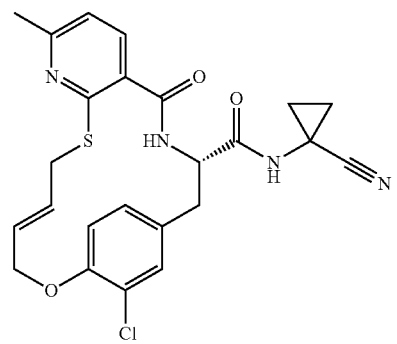 [SMILES: Cc1ccc2c(n1)SC/C=C/COc1ccc(cc1Cl)C[C@@H](C(=O)NC1(C#N)CC1)NC2=O]

The title compound was prepared in analogy to example 8 starting from 2-(allylthio)-6-methylnicotinic acid with the exception of the macroccyclisation: in a 10 mL round-bottomed flask, (S)—N-(3-(4-(allyloxy)-3-chlorophenyl)-1-(1-cyanocyclopropylamino)-1-oxopropan-2-yl)-2-(allylthio)-6-methylnicotinamide (50 mg, 97.8 μmol, Eq: 1.00) was combined with dry degassed DCM (50 mL) under argon atmosphere and titanium (IV) isopropoxide (16.7 mg, 17.2 μL, 58.7 μmol, Eq: 0.60) was added. This solution was added dropwise (20 min) to a solution of Grubbs II (24.9 mg, 29.4 μmol, Eq: 0.30) dissolved in dry degassed DCM (35 ml) under argon atmosphere at 50° C. (reflux). After the addition, the reaction mixture was heated to 50° C. and stirred for 3 days under argon atmosphere. The crude material was purified by flash chromatography (silica gel, 20 g, n-heptane/AcOEt 2/1, 1/1) to yield a brown solid (4 mg; 6%). m/z=483.0 [M+H]⁺.

Example 20

(E)-(S)-19-Chloro-5-oxo-9-trifluoromethyl-12,17-dioxa-4-aza-tricyclo[16.2.2.0*6,11*]docosa-1(21),6,8,10,14,18(22),19-heptaene-3-carboxylic acid (1-cyano-cyclopropyl)-amide

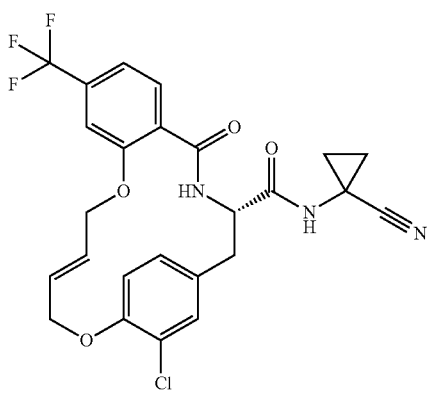 [SMILES: N#CC1(NC(=O)[C@@H]2Cc3ccc(c(Cl)c3)OC/C=C/COc3cc(C(F)(F)F)ccc3C(=O)N2)CC1]

A) 2-(Allyloxy)-4-(trifluoromethyl)benzoic acid

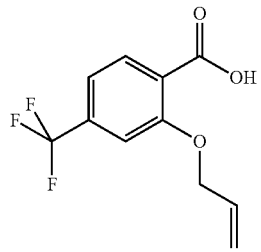 [SMILES: C=CCOc1cc(C(F)(F)F)ccc1C(=O)O]

In a 25 mL round-bottomed flask, 2-hydroxy-4-(trifluoromethyl)benzoic acid (300 mg, 1.46 mmol, Eq: 1.00) was combined with acetonitrile (3.00 mL). K₂CO₃ (503 mg, 3.64 mmol, Eq: 2.50) and 3-bromoprop-1-ene (454 mg, 325 µL, 3.64 mmol, Eq: 2.50) were added. The reaction mixture was heated to 80° C. and stirred for 3 h. The solvent was evaporated. The crude reaction mixture was poured into water and extracted with DCM (2×). The organic layers were dried over Na₂SO₄ and concentrated in vacuo. 2-Allyloxy-4-trifluoromethyl-benzoic acid allyl ester (433 mg) was recovered. The crude bisalkylated product was combined with ethanol (2.5 mL) and water (0.5 mL) and sodium hydroxide (116 mg, 2.91 mmol, Eq: 2.00) was added. The reaction mixture was heated to 80° C. and stirred for 16 h. The crude reaction mixture was concentrated in vacuo. The reaction mixture was treated with aqueous 1M HCl solution until pH=1-2 was reached. After that, the mixture was extracted with DCM (3×). The organic layers were dried over Na₂SO₄ and concentrated in vacuo to yield a light yellow solid (296 mg; 83% two steps). m/z=245.2 [M−H]⁻.

B) E)-(S)-19-Chloro-5-oxo-9-trifluoromethyl-12,17-dioxa-4-aza-tricyclo[16.2.2.0*6,11*]docosa-1(21),6,8,10,14,18(22), 19-heptaene-3-carboxylic acid (1-cyano-cyclopropyl)-amide

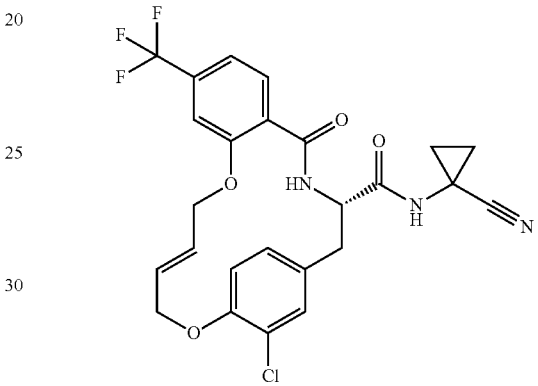

The title compound was prepared in analogy to example 8 starting from example 20A) to yield a brown solid (112 mg; 49%). m/z=520.2 [M+H]⁺.

Example 21

(E)-(S)-19-Chloro-5-oxo-17-oxa-4,12-diaza-tricyclo[16.2.2.0*6,11*]docosa-1(21),6,8,10,14,18(22),19-heptaene-3-carboxylic acid (1-cyano-cyclopropyl)-amide

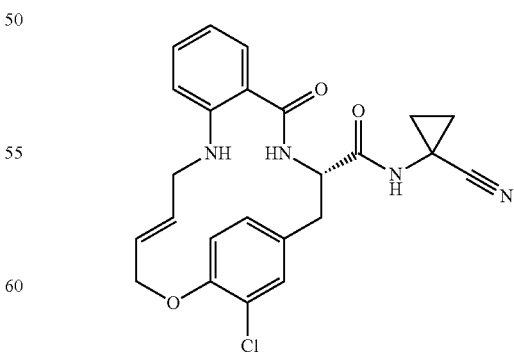

The title compound was prepared in analogy to example 19 starting from 2-allylamino-benzoic acid to yield a light grey solid (5 mg; 9%). m/z=451.0 [M+H]⁺.

Example 22

(S)-19-Chloro-9-methoxy-5-oxo-17-oxa-4-aza-tricyclo[16.2.2.0*6,11*]docosa-1(21),6,8,10,18(22),19-hexaene-3-carboxylic acid (1-cyano-cyclopropyl)-amide

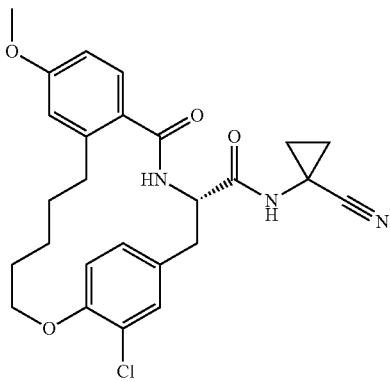 [SMILES: COc1ccc2c(c1)CCCCCOc1ccc(cc1Cl)C[C@@H](C(=O)NC1(C#N)CC1)NC2=O]

The title compound was prepared in analogy to example 9 starting from example 18 to yield an off-white solid (10 mg; 33%). m/z=482.3 [M+H]$^+$.

Example 23

(S)-19-Chloro-5-oxo-9-trifluoromethyl-12,17-dioxa-4-aza-tricyclo[16.2.2.0*6,11*]docosa-1(21),6,8,10,18(22),19-hexaene-3-carboxylic acid (1-cyano-cyclopropyl)-amide

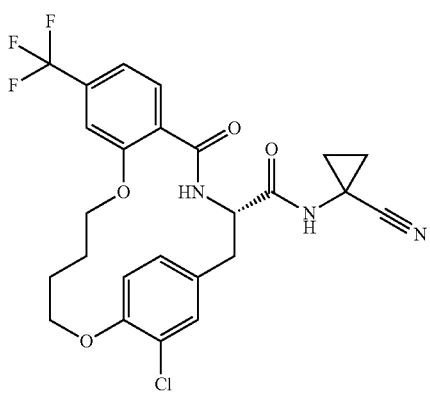 [SMILES: N#CC1(NC(=O)[C@@H]2Cc3ccc(c(Cl)c3)OCCCCOc3cc(C(F)(F)F)ccc3C(=O)N2)CC1]

The title compound was prepared in analogy to example 9 starting from example 20 to yield a grey solid (20 mg; 22%). m/z=522.3 [M+H]$^+$.

Example 24

(E)-(S)-19-Iodo-5-oxo-12,17-dioxa-4-aza-tricyclo[16.2.2.*6,11*]docosa-1(21),6,8,10,14,18(22),19-heptaene-3-carboxylic acid (1-cyano-cyclopropyl)-amide

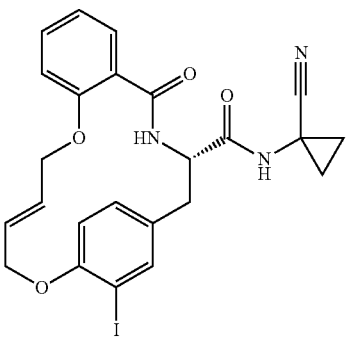 [SMILES: N#CC1(NC(=O)[C@@H]2Cc3ccc(c(I)c3)OC/C=C/COc3ccccc3C(=O)N2)CC1]

The title compound was prepared in analogy to example 4 to yield a brown solid (130 mg; 41%) as atropisomeric mixture. m/z=544.1 [M+H]$^+$.

Example 25

(E)-(S)-19-Iodo-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide, stereoaxis R

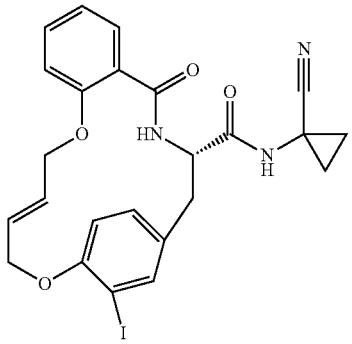 [SMILES: N#CC1(NC(=O)[C@@H]2Cc3ccc(c(I)c3)OC/C=C/COc3ccccc3C(=O)N2)CC1]

The title compound was obtained after chiral chromatography to yield an off-white solid (2 mg; 17%). m/z=544.1 [M+H]$^+$.

Example 26

(E)-(S)-19-Iodo-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide, stereoaxis S

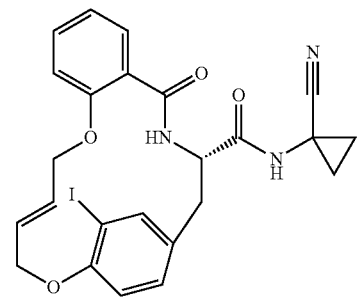 [SMILES: N#CC1(NC(=O)[C@@H]2Cc3ccc(c(I)c3)OC/C=C/COc3ccccc3C(=O)N2)CC1]

The title compound was obtained after chiral chromatography to yield an off-white solid (2 mg; 17%). m/z=544.1 [M+H]$^+$.

Example 27

(3E,12S)-22-chloro-N-(1-cyanocyclopropyl)-14-oxo-2,5,11,12,13,14,16,17,18,19-decahydro-7,10-ethenonaphtho[2,3-b][1,12,5]dioxazacyclohexadecine-12-carboxamide

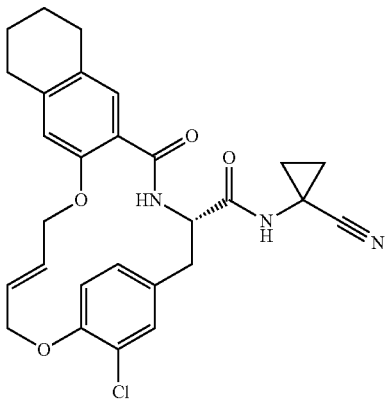 [SMILES: N#CC1(NC(=O)[C@@H]2Cc3ccc(c(Cl)c3)OC/C=C/COc3cc4c(cc3C(=O)N2)CCCC4)CC1]

The title compound was prepared in analogy to example 20 starting from 3-hydroxy-5,6,7,8-tetrahydro-naphthalene-2-carboxylic acid to yield a brown solid (58 mg; 33%). m/z=506.2 [M+H]$^+$.

Example 28

(E)-(S)-8-Chloro-19-iodo-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide

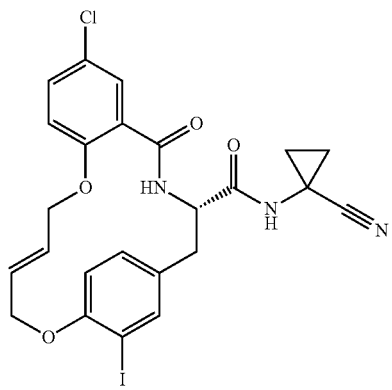 [SMILES: N#CC1(NC(=O)[C@@H]2Cc3ccc(c(I)c3)OC/C=C/COc3ccc(Cl)cc3C(=O)N2)CC1]

The title compound was prepared in analogy to example 20 starting from 2-allyloxy-4-chloro-benzoic acid to yield a brown solid (62 mg; 55%). m/z=578.2 [M+H]$^+$.

Example 29

(12S)-22-chloro-N-(1-cyanocyclopropyl)-14-oxo-2,3,4,5,11,12,13,14,16,17,18,19-dodecahydro-7,10-ethenonaphtho[2,3-b][1,12,5]dioxazacyclohexadecine-12-carboxamide

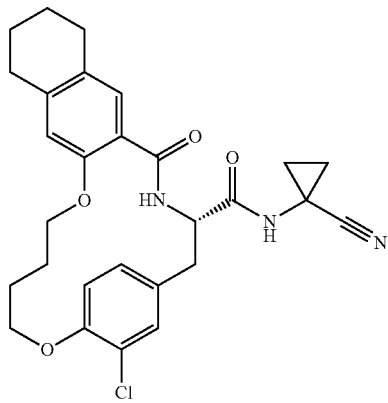 [SMILES: N#CC1(NC(=O)[C@@H]2Cc3ccc(c(Cl)c3)OCCCCOc3cc4c(cc3C(=O)N2)CCCC4)CC1]

The title compound was prepared in analogy to example 9 starting from example 27 to yield a light brown solid (20 mg; 50%). m/z=508.3 [M+H]$^+$.

Example 30

(S)-19-Iodo-5-oxo-12,17-dioxa-4-aza-tricyclo[16.2.2.0*6,11*]docosa-1(21),6(11),7,9,18(22),19-hexaene-3-carboxylic acid (1-cyano-cyclopropyl)-amide

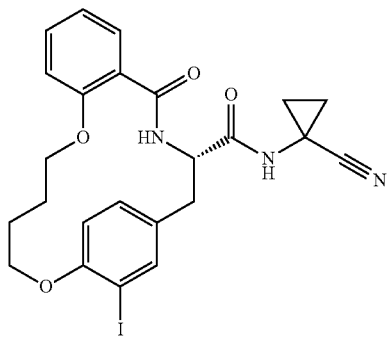 [SMILES: N#CC1(NC(=O)[C@@H]2Cc3ccc(c(I)c3)OCCCCOc3ccccc3C(=O)N2)CC1]

Example 24 (20 mg, 36.8 µmol, Eq: 1.00) and Raney Nickel (9.99 mg, 79.1 µmol, Eq: 2.15) were combined with ethyl acetate (2 mL) and stirred under a hydrogen atmosphere at 50° C. and 10 bar for 20 h. The crude reaction mixture was filtered and evaporated to dryness to yield a light brown solid (17 mg; 68%) as mixture of atropisomers. m/z=544.0741 $[M+H]^+$.

Example 31

(S)-8-Chloro-19-iodo-5-oxo-12,17-dioxa-4-aza-tricyclo[16.2.2.0*6,11*]docosa-1(21),6(11),7,9,18(22),19-hexaene-3-carboxylic acid (1-cyano-cyclopropyl)-amide

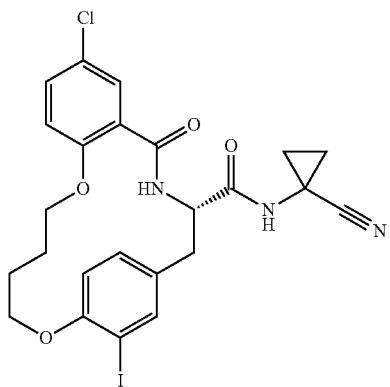 [SMILES: N#CC1(NC(=O)[C@@H]2Cc3ccc(c(I)c3)OCCCCOc3ccc(Cl)cc3C(=O)N2)CC1]

The title compound was prepared in analogy to example 30 starting from example 24 to yield a light brown solid (17 mg; 68%) as mixture of atropisomers. m/z=578.0352 $[M+H]^+$.

Example 32

(E)-(S)-19-Chloro-8-fluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide

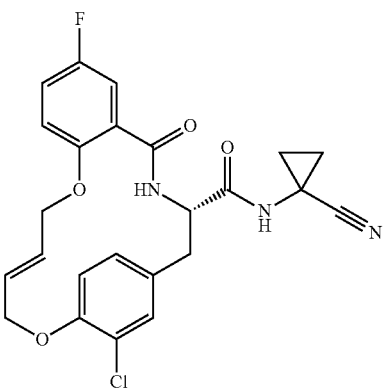 [SMILES: N#CC1(NC(=O)[C@@H]2Cc3ccc(c(Cl)c3)OC/C=C/COc3ccc(F)cc3C(=O)N2)CC1]

The title compound was prepared in analogy to example 20 starting from 5-fluoro-2-hydroxy-benzoic acid to yield a brown solid (98 mg; 57%). m/z=470.4 $[M+H]^+$.

Example 33

(E)-(S)-9,19-Dichloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide

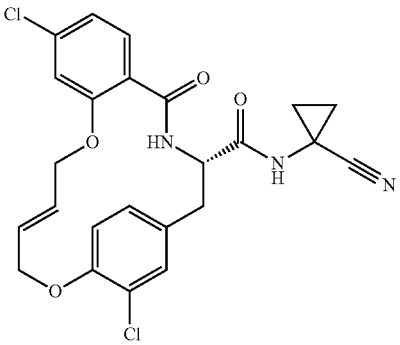 [SMILES: N#CC1(NC(=O)[C@@H]2Cc3ccc(c(Cl)c3)OC/C=C/COc3cc(Cl)ccc3C(=O)N2)CC1]

The title compound was prepared in analogy to example 20 starting from 2-allyloxy-4-chloro-benzoic acid to yield a brown solid (92 mg; 41%). m/z=486.3 $[M+H]^+$.

Example 34

(E)-(S)-19-Chloro-5-oxo-8-trifluoromethyl-12,17-dioxa-4-aza-tricyclo[16.2.2.0*6,11*]docosa-1(21),6,8,10,14,18(22),19-heptaene-3-carboxylic acid (1-cyano-cyclopropyl)-amide

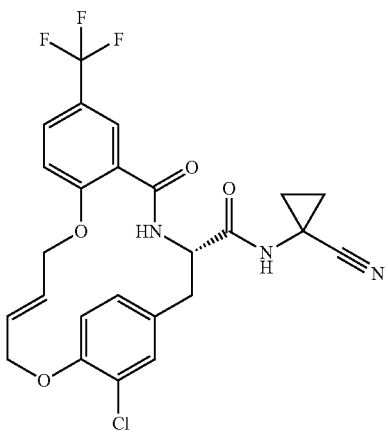 [SMILES: N#CC1(NC(=O)[C@@H]2Cc3ccc(c(Cl)c3)OC/C=C/COc3ccc(C(F)(F)F)cc3C(=O)N2)CC1]

The title compound was prepared in analogy to example 20 starting from 2-allyloxy-5-trifluoromethyl-benzoic acid to yield a brown solid (92 mg; 36%). m/z=520.3 [M+H]⁺.

Example 35

(S)-19-Chloro-8-fluoro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide

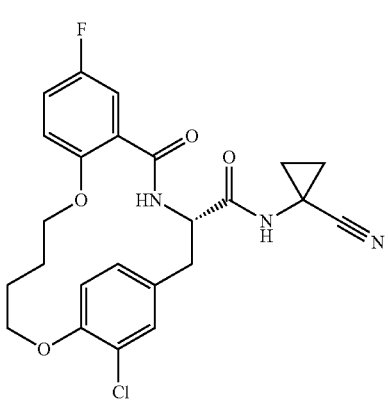 [SMILES: N#CC1(NC(=O)[C@@H]2Cc3ccc(c(Cl)c3)OCCCCOc3ccc(F)cc3C(=O)N2)CC1]

The title compound was prepared in analogy to example 9 starting from example 32 to yield a light brown solid (20 mg; 62%). m/z=472.3 [M+H]⁺.

Example 36

(S)-9,19-Dichloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide

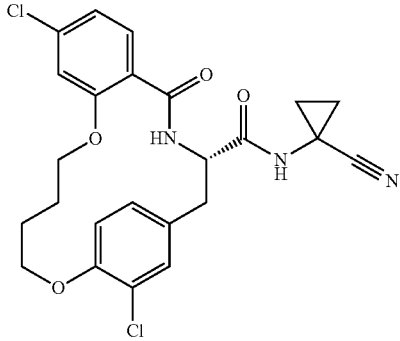 [SMILES: N#CC1(NC(=O)[C@@H]2Cc3ccc(c(Cl)c3)OCCCCOc3cc(Cl)ccc3C(=O)N2)CC1]

The title compound was prepared in analogy to example 9 starting from example 33 to yield a light brown solid (29 mg; 72%). m/z=488.2 [M+H]⁺.

Example 37

(S)-19-Chloro-5-oxo-8-trifluoromethyl-12,17-dioxa-4-aza-tricyclo[16.2.2.0*6,11*]docosa-1(21),6,8,10,18(22),19-hexaene-3-carboxylic acid (1-cyano-cyclopropyl)-amide

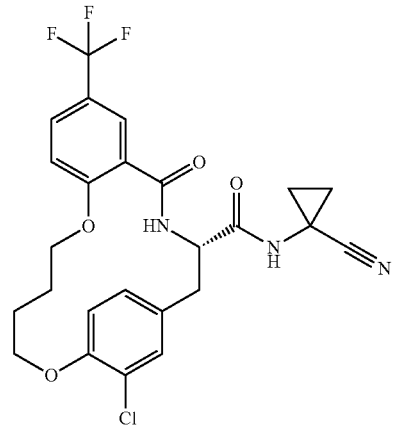 [SMILES: N#CC1(NC(=O)[C@@H]2Cc3ccc(c(Cl)c3)OCCCCOc3ccc(C(F)(F)F)cc3C(=O)N2)CC1]

The title compound was prepared in analogy to example 9 starting from example 34 to yield a light brown solid (39 mg; 86%). m/z=522.4 [M+H]⁺.

Example 38

(E)-(S)-8-Bromo-19-chloro-5-oxo-17-oxa-4,12-diaza-tricyclo[16.2.2.0*6,11*]docosa-1(21),6,8,10,14,18(22),19-heptaene-3-carboxylic acid (1-cyano-cyclopropyl)-amide

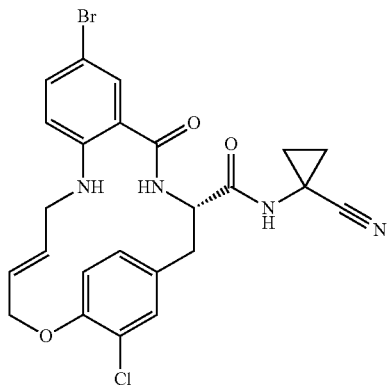 [SMILES: N#CC1(NC(=O)[C@@H]2Cc3ccc(c(Cl)c3)OC/C=C/CNc3ccc(Br)cc3C(=O)N2)CC1]

The title compound was prepared in analogy to example 19 starting from 2-allylamino-5-bromo-benzoic acid to yield a light brown solid (8 mg; 4%). m/z=531.0610 [M+H]$^+$.

Example 39

3-[(E)-(S)-19-Chloro-3-(1-cyano-cyclopropylcarbamoyl)-5-oxo-12,17-dioxa-4-aza-tricyclo[16.2.2.0*6,11*]docosa-1(21),6,8,10,14,18(22),19-heptaen-8-yl]-azetidine-1-carboxylic acid tert-butyl ester

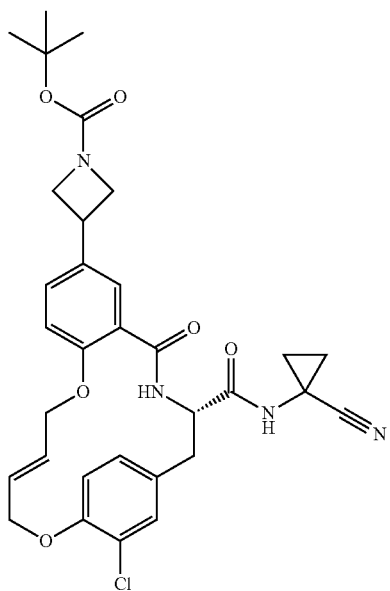 [SMILES: CC(C)(C)OC(=O)N1CC(c2ccc3c(c2)C(=O)N[C@H](C(=O)NC2(C#N)CC2)Cc2ccc(c(Cl)c2)OC/C=C/CO3)C1]

A) 3-(4-Allyloxy-3-carboxy-phenyl)-azetidine-1-carboxylic acid tert-butyl ester

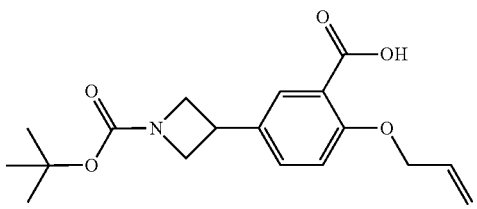 [SMILES: C=CCOc1ccc(C2CN(C(=O)OC(C)(C)C)C2)cc1C(=O)O]

Example 39A) was prepared in analogy to example 20A) starting from commercially available 3-(3-carboxy-4-hydroxy-phenyl)-azetidine-1-carboxylic acid tert-butyl ester to yield the title compound as a light yellow oil (18 mg; 100%). m/z=332.3 [M−H]$^-$.

B) 3-[(E)-(S)-19-Chloro-3-(1-cyano-cyclopropylcarbamoyl)-5-oxo-12,17-dioxa-4-aza-tricyclo[16.2.2.0*6,11*]docosa-1 (24),6,8,10,14,18(22),19-heptaen-8-yl]-azetidine-1-carboxylic acid tert-butyl ester

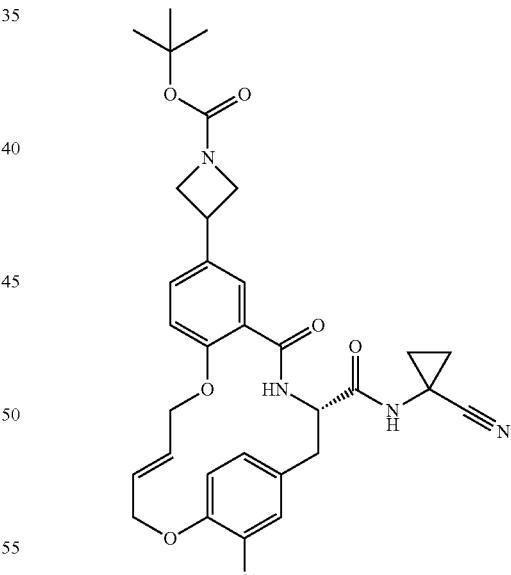

Example 39B was prepared in analogy to the methods described for examples 8C-D) starting from example 13E) and example 39A) to yield the title compound as a brown solid (104 mg; 50%). m/z=607.2 [M+H]$^+$.

Example 40

(E)-(S)-19-Chloro-8-cyano-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide

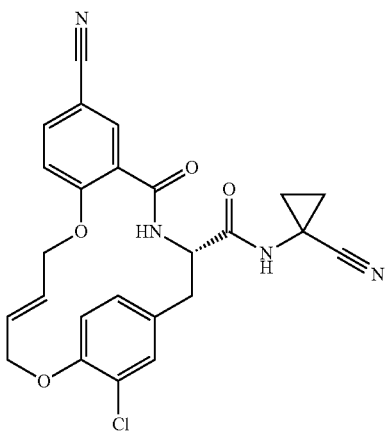 [SMILES: N#Cc1ccc2c(c1)C(=O)N[C@H](C(=O)NC1(C#N)CC1)Cc1ccc(c(Cl)c1)OC/C=C/CO2]

Example 40 was prepared in analogy to the methods described for examples 8C-D) starting from example 13E) and 2-allyloxy-5-cyano-benzoic acid (prepared in analogy to example 20A)) to yield the title compound as a brown solid (104 mg; 50%). m/z=607.2 [M+H]$^+$.

Example 41

(E)-(S)-8-Azetidin-3-yl-19-chloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide

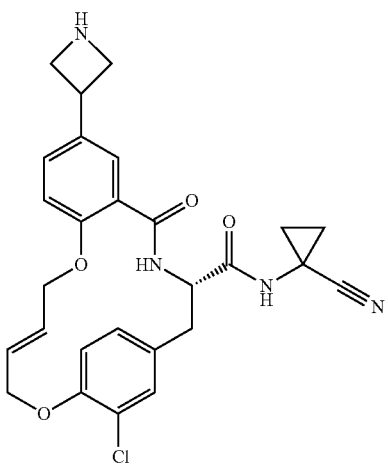 [SMILES: N#CC1(NC(=O)[C@@H]2Cc3ccc(c(Cl)c3)OC/C=C/COc3ccc(C4CNC4)cc3C(=O)N2)CC1]

In a 5 ml round-bottomed flask, example 39B) (20 mg, 32.9 μmol, Eq: 1.00) was combined with formic acid (227 mg, 190 μl, 4.94 mmol, Eq: 150). The reaction mixture was stirred at 22° C. for 2 h. The reaction mixture was quenched with aqueous 5% Na$_2$CO$_3$ solution until pH=10-12 was reached and extracted with DCM (4×50 ml). The organic layers were dried over Na$_2$SO$_4$ and concentrated in vacuo.
The crude material was purified by flash chromatography (silica gel, 5 g, DCM/MeOH 98/2, 9/1, DCM/MeOH/NH$_4$OH 90/9/1) to yield the title compound as a light brown solid (10 mg; 60%). m/z=507.3 [M+H]$^+$.

Example 42

3-[(S)-19-Chloro-3-(1-cyano-cyclopropylcarbamoyl)-5-oxo-12,17-dioxa-4-aza-tricyclo[16.2.2.0*6,11*]docosa-1(21),6,8,10,18(22),19-hexaen-8-yl]-azetidine-1-carboxylic acid tert-butyl ester

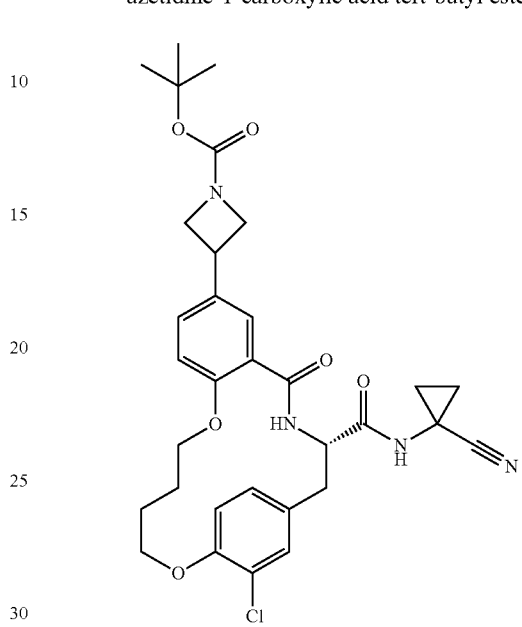

Example 42 was prepared in analogy to example 9 to yield the title compound as a brown solid as a mixture of atropisomers (68 mg; 94%). m/z=609.2 [M+H]$^+$.

Example 43

(S)-8-Azetidin-3-yl-19-chloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide

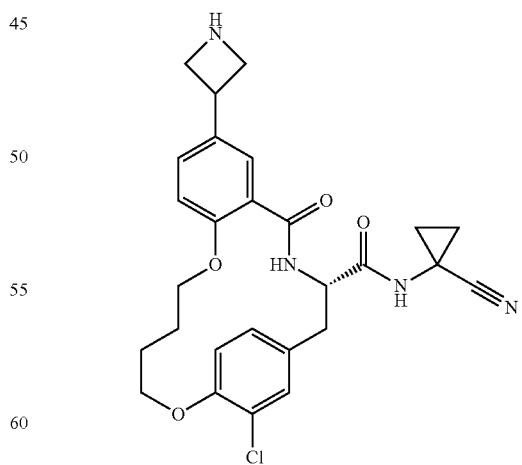

Example 43 was prepared in analogy to example 41 starting from example 42 to yield the title compound as a white solid as a mixture of atropisomers (22 mg; 53%). m/z=509.4 [M+H]$^+$.

Example 44

(E-Z)—(S)-19-Chloro-8,10-difluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide

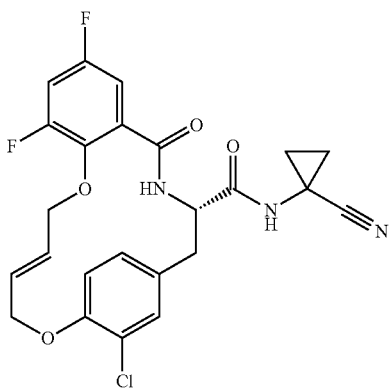 [SMILES: N#CC1(NC(=O)[C@@H]2Cc3ccc(c(Cl)c3)OC/C=C/COc3c(F)cc(F)cc3C(=O)N2)CC1]

Example 44 was prepared in analogy to the methods described for examples 8C-D) starting from example 13E) and 2-allyloxy-3,5-difluoro-benzoic acid (prepared in analogy to example 20A)) to yield the title compound as a brown solid (13 mg; 8%). m/z=488.1 [M+H]$^+$.

Example 45

(E)-(S)-19-Chloro-7,8-difluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide

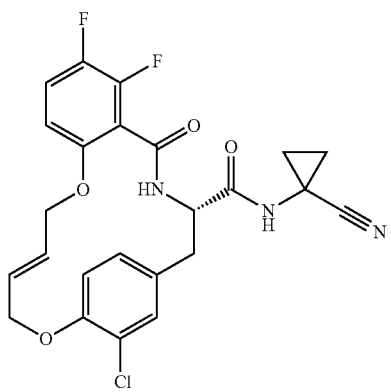 [SMILES: N#CC1(NC(=O)[C@@H]2Cc3ccc(c(Cl)c3)OC/C=C/COc3ccc(F)c(F)c3C(=O)N2)CC1]

Example 45 was prepared in analogy to the methods described for examples 8C-D) starting from example 13E) and 6-allyloxy-2,3-difluoro-benzoic acid (prepared in analogy to example 20A)) to yield the title compound as a brown solid (41 mg; 25%). m/z=488.2 [M+H]$^+$.

Example 46

(Z)—(S)-19-Chloro-7,8-difluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide

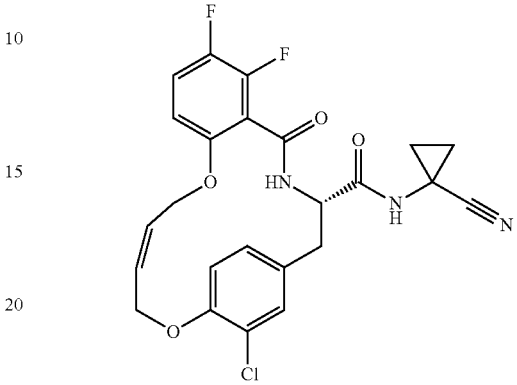

Example 46 was obtained as a by-product throughout the synthesis of example 45 to yield the title compound as a brown solid (24 mg; 15%). m/z=488.2 [M+H]$^+$.

Example 47

(E)-(S)-19-Chloro-8-methylsulfanyl-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide

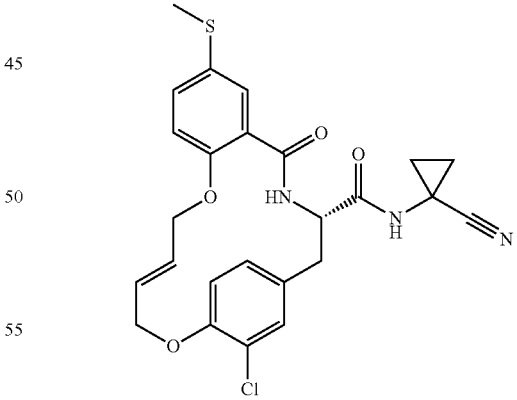

Example 47 was prepared in analogy to the methods described for examples 8C-D) starting from example 13E) and 2-allyloxy-5-methylsulfanyl-benzoic acid (prepared in analogy to example 20A)) to yield the title compound as a brown solid (58 mg; 54%). m/z=498.2 [M+H]$^+$.

Example 48

(E)-(S)-10,19-Dichloro-8-fluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide

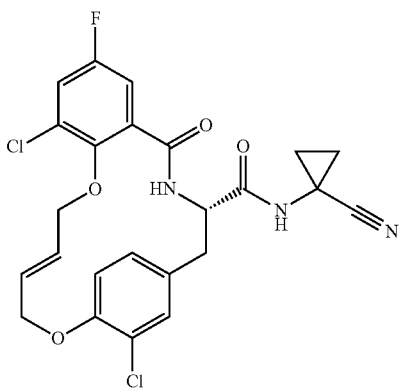 [SMILES: N#CC1(NC(=O)[C@@H]2Cc3ccc(c(Cl)c3)OC/C=C/COc3c(Cl)cc(F)cc3C(=O)N2)CC1]

Example 48 was prepared in analogy to the methods described for examples 8C-D) starting from example 13E) and 2-allyloxy-3-chloro-5-fluoro-benzoic acid (prepared in analogy to example 20A)) to yield the title compound as a mixture of atropisomers and as a brown solid (5 mg; 3%). m/z=504.1 [M+H]$^+$.

Example 49

(S)-19-Chloro-8-cyano-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide

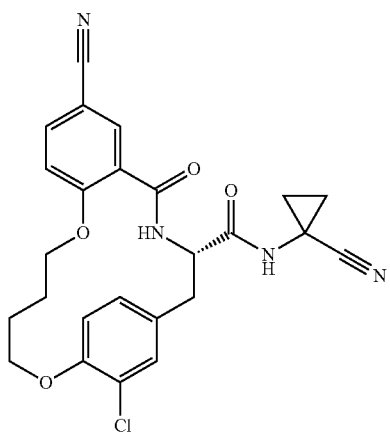 [SMILES: N#Cc1ccc2c(c1)C(=O)N[C@H](C(=O)NC1(C#N)CC1)Cc1ccc(c(Cl)c1)OCCCCO2]

Example 49 was prepared in analogy to example 9 starting from example 40 to yield the title compound as a brown solid (6 mg; 45%). m/z=477.1343 [M−H]$^-$.

Example 50

(S)-19-Chloro-7,8-difluoro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide

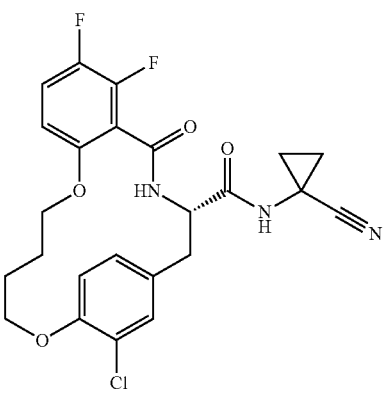 [SMILES: N#CC1(NC(=O)[C@@H]2Cc3ccc(c(Cl)c3)OCCCCOc3ccc(F)c(F)c3C(=O)N2)CC1]

Example 50 was prepared in analogy to example 9 starting from example 45 to yield the title compound as a brown solid as a mixture of atropsiomers (18 mg; 45%). m/z=490.1339 [M+H]$^+$.

Example 51

(S)-19-Chloro-8-methylsulfanyl-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide Example 51 was prepared in analogy to example 9 starting from example 47 to yield the title compound as a brown solid as a mixture of atropsiomers (3.3 mg; 9%). m/z=500.1404 [M+H]$^+$.

Example 52

Cathepsin Enzyme Inhibition Assay

Enzyme activity is measured by observing the increase in fluorescence intensity caused by cleavage of a peptide substrate containing a fluorophore whose emission is quenched in the intact peptide.

Assay buffer: 100 mM potassium phosphate pH 6.5, EDTA-Na 5 mM, Triton X-100 0.001%, DDT 5 mM.
Enzymes (all at 1 nM): human and mouse Cathepsin S, Cat K, Cat B, Cat L
Substrate (20 µM): Z-Val-Val-Arg-AMC, except for Cat K which uses Z-Leu-Arg-AMC (both from Bachem).
Z=Benzyloxycarbonyl.
AMC=7-Amino-4-Methyl-Coumarin.
Final volume: 100 µL.
Excitation 360 nm, Emission 465 nm.
Enzyme is added to the substance dilutions in 96-well microtitre plates and the reaction is started with substrate. Fluorescence emission is measured over 20 minutes, during which time a linear increase is observed in the absence of inhibitor. $IC_{50}$ are calculated by standard methods. The results are expressed in µM in the following table.

In the foregoing assay, the compounds according to the invention have an $IC_{50}$ for Cathepsin L which is between 0.00001 and 200 µM. $IC_{50}$ for particular compounds is between 0.00001 and 100 µM, more particularly between 0.00001 and 80 µM.

Furthermore, particular compounds of the invention have a selectivity for Cathepsin L inhibition over the other Cathepsins, and in particular over Cathepsin S, of more than 10-fold.

The results obtained for selected compounds of formula (I) in the above cathepsin L assay are shown in the following table.

| Example | IC50 (uM) |
|---|---|
| 1 | 0.0885 |
| 2 | 0.23 |
| 3 | 0.077 |
| 4 | 0.0138 |
| 5 | 0.0096 |
| 6 | 0.032 |
| 7 | 0.0962 |
| 8 | 0.0248 |
| 9 | 0.01 |
| 10 | 0.0103 |
| 11 | 0.0116 |
| 12 | 0.878 |
| 13 | 0.9482 |
| 14 | 6.0635 |
| 15 | 0.1676 |
| 16 | 0.0114 |
| 17 | 0.0104 |
| 18 | 0.0547 |
| 19 | 0.026 |
| 20 | 0.0477 |
| 21 | 0.054 |
| 22 | 0.1184 |
| 23 | 0.05 |
| 24 | 0.1638 |
| 25 | 0.2356 |
| 26 | 0.1391 |
| 27 | 0.016 |
| 28 | 0.011 |
| 29 | 0.013 |
| 30 | 0.181 |
| 31 | 0.012 |
| 32 | 0.016 |
| 33 | 0.073 |
| 34 | 0.009 |
| 35 | 0.023 |
| 36 | 0.05 |
| 37 | 0.009 |
| 38 | 0.01 |
| 39 | 0.0262 |
| 40 | 0.0069 |
| 41 | 0.0052 |
| 42 | 0.0255 |
| 43 | 0.0031 |
| 44 | 0.0092 |
| 45 | 0.0043 |
| 46 | 0.054 |
| 47 | 0.0016 |
| 48 | 0.1386 |
| 49 | 0.0183 |
| 50 | 0.0135 |
| 51 | 0.0016 |

Example A

Film Coated Tablets Containing the Following Ingredients can be Manufactured in a Conventional Manner

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules Containing the Following Ingredients can be Manufactured in a Conventional Manner

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection Solutions can have the Following Composition

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:
1. A compound of formula (I)

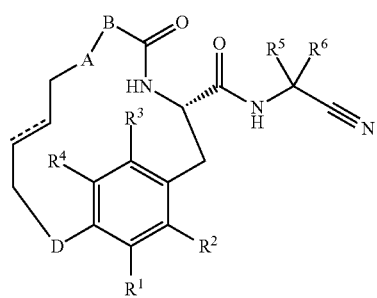

(I)

wherein
A is —O—, —S—, —CH$_2$—, —NH— or —SO$_2$—;
B is phenyl, substituted phenyl, pyrrolidinyl, substituted pyrrolidinyl, pyridinyl, substituted pyridinyl, pyrimidinyl, substituted pyrimidinyl, 1,2,3,4-tetrahydronaphtalenyl, bicyclo[4.2.0]octa-1(6),2,4-trienyl, indanyl or 6,7,8,9-tetrahydro-5H-benzocycloheptenyl, wherein substituted phenyl is phenyl substituted with one or two substituents each of which is independently halogen, alkyl, cyclopropyl, cyclobutyl, cyclopentyl, cyclohexyl, cycloheptyl, cyclooctyl, alkoxy, haloalkyl, azetidinyl, alkylsulfanyl or cyano, wherein substituted pyrrolidinyl is pyrrolidinyl substituted with one or two substituents each of which is independently halogen, alkyl, alkoxy, haloalkoxy, cyclopropyl, cyclobutyl, cyclopentyl, cyclohexyl, cycloheptyl, cyclooctyl, alkylsulfanyl, alkylsulfonyl, cyclopropylsulfanyl, cyclobutylsulfanyl, cyclopentylsulfanyl, cyclohexylsulfanyl, cycloheptylsulfanyl, cyclooctylsulfanyl, cyclopropylsulfonyl, cyclobutylsulfonyl, cyclopentylsulfonyl, cyclohexylsulfonyl, cycloheptylsulfonyl and cyclooctylsulfonyl, wherein substituted pyridinyl is pyridinyl substituted with halogen, alkyl, cyclopropyl, cyclobutyl, cyclopentyl, cyclohexyl, cycloheptyl, cyclooctyl, alkoxy or haloalkoxy, and wherein substituted pyrimidinyl is pyrimidinyl substituted with halogen, alkyl, cyclopropyl, cyclobutyl, cyclopentyl, cyclohexyl, cycloheptyl, cyclooctyl, alkoxy or haloalkoxy;

D is —O—, —S—, —CH$_2$—, —NH— or —SO$_2$—;
one of R$^1$, R$^2$, R$^3$ and R$^4$ is hydrogen and the other ones are independently selected from hydrogen, halogen, alkyl, alkoxy, haloalkoxy, cyclopropyl, cyclobutyl, cyclopentyl, cyclohexyl, cycloheptyl, cyclooctyl and phenyl;
or R$^5$ and R$^6$ together with the carbon atom to which they are attached form cyclopropyl; and
---- is a carbon-carbon single bond or a carbon-carbon double bond;
or a pharmaceutically acceptable salt or ester thereof.
2. A compound according to claim 1, wherein A is —O—, —S—, —CH$_2$— or —NH—.
3. A compound according to any one of claims 1 or 2, wherein B is phenyl, halophenyl, pyrrolidinyl, halopyrrolidinyl, alkylpyrrolidinyl, alkoxyphenyl, alkylpyrridinyl, haloalkylphenyl, tetrahydronaphtyl, azetidinylphenyl, cyanophenyl or alkylsulfanylphenyl.
4. A compound according to claim 1, wherein B is phenyl, bromophenyl, chlorophenyl, difluorophenyl, methoxyphenyl or methylpyridinyl, trifluoromethylphenyl, azetidinylphenyl, cyanophenyl or methylsulfanylphenyl.
5. A compound according to claim 1, wherein D is —O—.
6. A compound according to claim 1, wherein one of R$^1$ and R$^4$ is hydrogen and the other one is halogen.
7. A compound according to claim 1, wherein one of R$^1$ and R$^4$ is hydrogen and the other one is bromo, chloro or iodo.
8. A compound according to claim 1, wherein R$^2$ and R$^3$ are both hydrogen.
9. A compound selected from
(E)-(S)-5-Oxo-12,17-dioxa-4-aza-tricyclo[16.2.2.0*6,11*]docosa-1(21),6(11),7,9,14,18(22),19-heptaene-3-carboxylic acid (1-cyano-cyclopropyl)-amide;
(E)-(S)-5-Oxo-11,16-dioxa-4-aza-tricyclo[15.2.2.1*6,10*]docosa-1(20),6,8,10(22),13,17(21),18-heptaene-3-carboxylic acid (1-cyano-cyclopropyl)-amide;
(E)-(S)-5-Oxo-17-oxa-4-aza-tricyclo[16.2.2.0*6,11*]docosa-1(21),6,8,10,14,18(22),19-heptaene-3-carboxylic acid (1-cyano-cyclopropyl)-amide;
(E)-(S)-19-Chloro-5-oxo-12,17-dioxa-4-aza-tricyclo[16.2.2.0*6,11*]docosa-1(21),6(11),7,9,14,18(22),19-heptaene-3-carboxylic acid (1-cyano-cyclopropyl)-amide;
(E)-(S)-19-Chloro-5-oxo-17-oxa-4-aza-tricyclo[16.2.2.0*6,11*]docosa-1(21),6,8,10,14,18(22),19-heptaene-3-carboxylic acid (1-cyano-cyclopropyl)-amide;
(E)-(S)-18-Chloro-5-oxo-11,16-dioxa-4-aza-tricyclo[15.2.2.1*6,10*]docosa-1(20),6,8,10(22),13,17(21),18-heptaene-3-carboxylic acid (1-cyano-cyclopropyl)-amide;
(S)-19-Chloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;
(E)-(S)-8-Bromo-19-chloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;
(S)-8-Bromo-19-chloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;
(E)-(S)-8,19-Dichloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-8,19-Dichloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E)-(S)-18-Chloro-5-oxo-16-oxa-4,10-diaza-tricyclo[15.2.2.0*6,10*]henicosa-1(20),13,17(21),18-tetraene-3-carboxylic acid (1-cyano-cyclopropyl)-amide;

(E)-(3S,8S)-18-Chloro-8-fluoro-5-oxo-16-oxa-4,10-diaza-tricyclo[15.2.2.0*6,10*]henicosa-1(20),13,17(21),18-tetraene-3-carboxylic acid (1-cyano-cyclopropyl)-amide;

(E)-(S)-18-Chloro-8,8-difluoro-5-oxo-16-oxa-4,10-diaza-tricyclo[15.2.2.0*6,10*]henicosa-1(20),13,17(21),18-tetraene-3-carboxylic acid (1-cyano-cyclopropyl)-amide;

(E)-(S)-18-Chloro-8,8-dimethyl-5-oxo-16-oxa-4,10-diaza-tricyclo[15.2.2.0*6,10*]henicosa-1(20),13,17(21),18-tetraene-3-carboxylic acid (1-cyano-cyclopropyl)-amide;

(E)-(S)-19-Chloro-8-methoxy-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-19-Chloro-8-methoxy-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E)-(S)-19-Chloro-9-methoxy-5-oxo-17-oxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-9-methyl-5-oxo-17-oxa-12-thia-4,10-diaza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-5-oxo-9-trifluoromethyl-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-5-oxo-17-oxa-4,12-diaza-tricyclo[16.2.2.0*6,11*]docosa-1(21),6,8,10,14,18(22),19-heptaene-3-carboxylic acid (1-cyano-cyclopropyl)-amide;

(S)-19-Chloro-9-methoxy-5-oxo-17-oxa-4-aza-tricyclo[16.2.2.0*6,11*]docosa-1(21),6,8,10,18(22),19-hexaene-3-carboxylic acid (1-cyano-cyclopropyl)-amide;

(S)-19-Chloro-5-oxo-9-trifluoromethyl-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E)-(S)-19-Iodo-5-oxo-12,17-dioxa-4-aza-tricyclo[16.2.2.*6,11*]docosa-1(21),6,8,10,14,18(22),19-heptaene-3-carboxylic acid (1-cyano-cyclopropyl)-amide;

(E)-(S)-19-Iodo-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide, stereoaxis R;

(E)-(S)-19-Iodo-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide, stereoaxis S;

(3E,12S)-22-chloro-N-(1-cyanocyclopropyl)-14-oxo-2,5,11,12,13,14,16,17,18,19-decahydro-7,10-ethenonaphtho[2,3-b][1,12,5]dioxazacyclohexadecine-12-carboxamide;

(E)-(S)-8-Chloro-19-iodo-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(12S)-22-chloro-N-(1-cyanocyclopropyl)-14-oxo-2,3,4,5,11,12,13,14,16,17,18,19-dodecahydro-7,10-ethenonaphtho[2,3-b][1,12,5]dioxazacyclohexadecine-12-carboxamide;

(S)-19-Iodo-5-oxo-12,17-dioxa-4-aza-tricyclo[16.2.2.0*6,11*]docosa-1(21),6(11),7,9,18(22),19-hexaene-3-carboxylic acid (1-cyano-cyclopropyl)-amide;

(S)-8-Chloro-19-iodo-5-oxo-12,17-dioxa-4-aza-tricyclo[16.2.2.0*6,11*]docosa-1(21),6(11),7,9,18(22),19-hexaene-3-carboxylic acid (1-cyano-cyclopropyl)-amide (E)-(S)-19-Chloro-8-fluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-9,19-Dichloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-5-oxo-8-trifluoromethyl-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-19-Chloro-8-fluoro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(S)-9,19-Dichloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(S)-19-Chloro-5-oxo-8-trifluoromethyl-12,17-dioxa-4-aza-tricyclo[16.2.2.0*6,11*]docosa-1(21),6,8,10,18(22),19-hexaene-3-carboxylic acid (1-cyano-cyclopropyl)-amide; and (E)-(S)-8-Bromo-19-chloro-5-oxo-17-oxa-4,12-diaza-tricyclo[16.2.2.0*6,11*]docosa-1(21),6,8,10,14,18(22),19-heptaene-3-carboxylic acid (1-cyano-cyclopropyl)-amide;

3-[(E)-(S)-19-Chloro-3-(1-cyano-cyclopropylcarbamoyl)-5-oxo-12,17-dioxa-4-aza-tricyclo[16.2.2.0*6,11*]docosa-1(21),6,8,10,14,18(22),19-heptaen-8-yl]-azetidine-1-carboxylic acid tert-butyl ester;

(E)-(S)-19-Chloro-8-cyano-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-8-Azetidin-3-yl-19-chloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

3-[(S)-19-Chloro-3-(1-cyano-cyclopropylcarbamoyl)-5-oxo-12,17-dioxa-4-aza-tricyclo[16.2.2.0*6,11*]docosa-1(21),6,8,10,18(22),19-hexaen-8-yl]-azetidine-1-carboxylic acid tert-butyl ester;

(S)-8-Azetidin-3-yl-19-chloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E-Z)—(S)-19-Chloro-8,10-difluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-7,8-difluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(Z)—(S)-19-Chloro-7,8-difluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-8-methylsulfanyl-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-10,19-Dichloro-8-fluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-19-Chloro-8-cyano-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(S)-19-Chloro-7,8-difluoro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide; and (S)-19-Chloro-8-methylsulfanyl-5-oxo-12,17-dioxa-4-aza-tricyclo[16.2.2.0*6,11*]docosa-1(21),6,8, 10,18(22),19-hexaene-3-carboxylic acid (1-cyano-cyclopropyl)-amide.

10. A compound according to claim 1, selected from
(E)-(S)-19-Chloro-5-oxo-12,17-dioxa-4-aza-tricyclo[16.2.2.0*6,11*]docosa-1(21),6(11),7,9,14,18(22),19-heptaene-3-carboxylic acid (1-cyano-cyclopropyl)-amide;

(E)-(S)-19-Chloro-5-oxo-17-oxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-18-Chloro-5-oxo-11,16-dioxa-4-aza-tricyclo[15.2.2.1*6,10*]docosa-1(20),6,8,10(22),13,17(21),18-heptaene-3-carboxylic acid (1-cyano-cyclopropyl)-amide;

(E)-(S)-8-Bromo-19-chloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-8-Bromo-19-chloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E)-(S)-8,19-Dichloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-8,19-Dichloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E)-(S)-19-Chloro-8-methoxy-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-19-Chloro-8-methoxy-5-oxo-12,17-dioxa-4-aza-tricyclo[16.2.2.0*6,11*]docosa-1(21),6,8, 10,18(22),19-hexaene-3-carboxylic acid (1-cyano-cyclopropyl)-amide;

(E)-(S)-19-Chloro-9-methyl-5-oxo-17-oxa-12-thia-4,10-diaza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-5-oxo-8-trifluoromethyl-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-19-Chloro-5-oxo-8-trifluoromethyl-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E)-(S)-19-Chloro-5-oxo-8-trifluoromethyl-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-19-Chloro-5-oxo-8-trifluoromethyl-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E)-(S)-8-Azetidin-3-yl-19-chloro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-8-Azetidin-3-yl-19-chloro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(E-Z)—(S)-19-Chloro-8,10-difluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-7,8-difluoro-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(E)-(S)-19-Chloro-8-methylsulfanyl-5-oxo-12,17-dioxa-4-aza-tricyclo[16.2.2.0*6,11*]docosa-1(21),6,8,10,14,18(22),19-heptaene-3-carboxylic acid (1-cyano-cyclopropyl)-amide;

(S)-19-Chloro-8-cyano-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide;

(S)-19-Chloro-7,8-difluoro-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide; and (S)-19-Chloro-8-methylsulfanyl-5-oxo-12,17-dioxa-4-aza-tricyclo[16.2.2.0*6,11*]docosa-1(21),6,8,10,18(22),19-hexaene-3-carboxylic acid (1-cyano-cyclopropyl)-amide.

11. A pharmaceutical composition comprising a compound in accordance with claim 1 and a therapeutically inert carrier.

* * * * *